United States Patent [19]

Hammerslag et al.

[11] Patent Number: 5,308,324
[45] Date of Patent: May 3, 1994

[54] STEERABLE MEDICAL DEVICE

[75] Inventors: Gary R. Hammerslag, Dana Point; Julius G. Hammerslag, San Juan Capistrano, both of Calif.

[73] Assignee: Pilot Cardiovascular Systems, Inc., San Clemente, Calif.

[21] Appl. No.: 32,681

[22] Filed: Mar. 17, 1993

Related U.S. Application Data

[60] Division of Ser. No. 865,357, Apr. 8, 1992, Pat. No. 5,203,772, which is a continuation-in-part of Ser. No. 583,819, Sep. 17, 1990, Pat. No. 5,108,368, which is a continuation-in-part of Ser. No. 461,049, Jan. 4, 1990, Pat. No. 4,998,916, which is a continuation-in-part of Ser. No. 295,124, Jan. 9, 1989, Pat. No. 4,921,482.

[51] Int. Cl.$^5$ .............................................. A61M 37/00
[52] U.S. Cl. ..................................... 604/95; 604/170; 606/191; 128/772
[58] Field of Search .......... 604/95, 164, 170, 280-283; 128/756, 757, 772, 657; 606/191-200

[56] References Cited

U.S. PATENT DOCUMENTS

| 33,166 | 2/1890 | Samson . |
|---|---|---|
| 3,470,876 | 10/1969 | Barchilon . |
| 3,521,620 | 7/1970 | Cook . |
| 3,547,103 | 12/1970 | Cook . |
| 3,605,725 | 9/1971 | Bentov . |
| 3,757,768 | 9/1973 | Kline . |
| 3,773,034 | 11/1973 | Burns et al. . |
| 4,456,017 | 6/1984 | Miles . |
| 4,538,622 | 9/1985 | Samson et al. . |
| 4,543,090 | 9/1985 | McCoy . |
| 4,545,390 | 10/1985 | Leary . |
| 4,554,929 | 11/1985 | Samson et al. . |
| 4,581,017 | 4/1986 | Sahota . |
| 4,582,181 | 4/1986 | Samson . |
| 4,616,653 | 10/1986 | Samson et al. . |
| 4,641,654 | 2/1987 | Samson et al. . |
| 4,650,466 | 3/1987 | Luther . |
| 4,654,024 | 3/1987 | Crittenden et al. . |
| 4,676,249 | 6/1987 | Arenas et al. . |
| 4,692,200 | 9/1987 | Powell . |
| 4,719,924 | 1/1988 | Crittenden et al. . |
| 4,721,117 | 1/1988 | Mar et al. . |
| 4,723,936 | 2/1988 | Buchbinder et al. . |
| 4,724,846 | 2/1988 | Evans, III . |
| 4,726,369 | 2/1988 | Mar . |
| 4,748,981 | 6/1988 | Crittenden . |
| 4,748,982 | 6/1988 | Horzewski et al. . |
| 4,753,223 | 6/1988 | Bremer . |
| 4,757,827 | 7/1988 | Buchbinder et al. . |
| 4,758,222 | 7/1988 | McCoy . |
| 4,763,647 | 7/1988 | Gambale . |
| 4,775,371 | 10/1988 | Mueller, Jr. . |
| 4,798,598 | 1/1989 | Bonello et al. . |
| 4,813,434 | 3/1989 | Buchbinder et al. . |
| 4,815,478 | 3/1989 | Buchbinder et al. . |
| 4,820,349 | 4/1989 | Saab . |
| 4,841,976 | 6/1989 | Packard et al. . |
| 4,846,186 | 7/1989 | Box et al. . |
| 4,877,031 | 10/1989 | Conway et al. . |
| 4,886,067 | 12/1989 | Palmero . |
| 4,892,519 | 1/1990 | Songer et al. . |
| 4,898,577 | 2/1990 | Badger et al. . |
| 4,940,062 | 7/1990 | Hampton et al. . |
| 5,024,654 | 6/1991 | Tyler . |
| 5,084,012 | 1/1992 | Kelman . |
| 5,106,381 | 4/1992 | Chikama . |
| 5,108,368 | 4/1992 | Hammerslag et al. . |
| 5,125,909 | 6/1992 | Heimberger . |
| 5,176,126 | 1/1993 | Chikama . |
| 5,195,968 | 3/1993 | Lundquist et al. . |

FOREIGN PATENT DOCUMENTS 265015 9/1991 France .
193885 1/1964 Sweden .

Primary Examiner—John D. Yasko
Attorney, Agent, or Firm—Darby & Darby

[57] ABSTRACT

A steering device, such as for use in a guidewire for percutaneous transluminal insertion into the coronary vascular system is provided. The guidewire comprises an elongate flexible housing having proximal and distal ends and at least one lumen extending through the length of the housing. The guidewire has a steering element secured within the lumen and adapted to displace the distal end of the housing in a lateral direction. At least one deflection wire extends through the flexible housing extending from a distal point of attachment to the proximal end. Axial movement of the deflection wire displaces a distal steering region of the housing in a lateral direction.

30 Claims, 9 Drawing Sheets

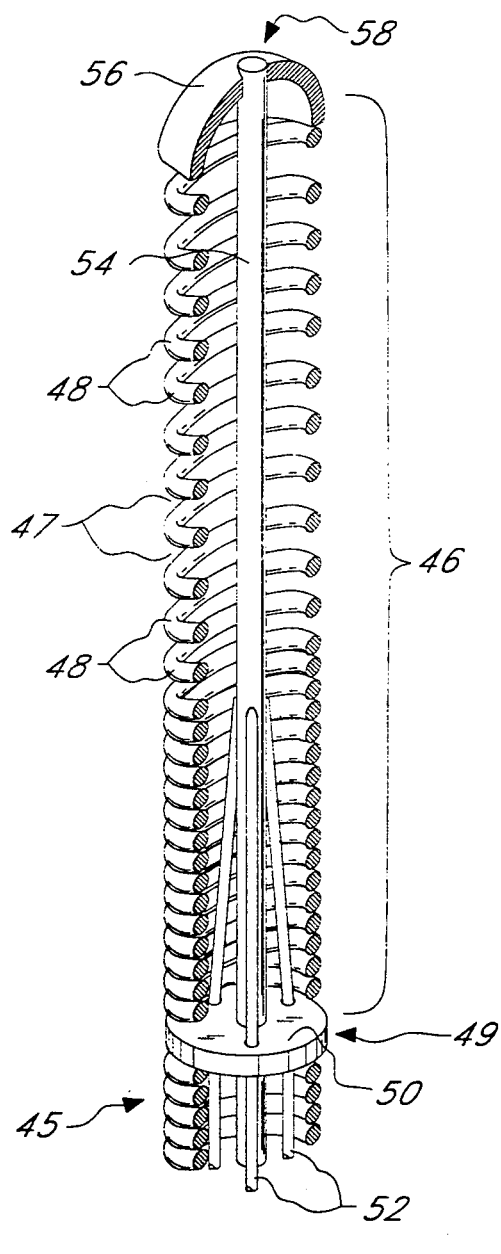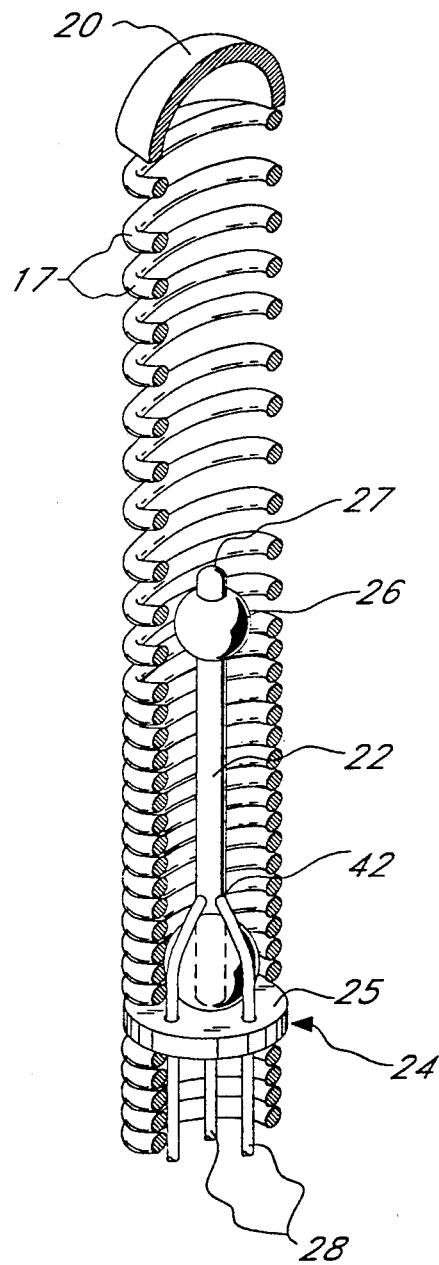

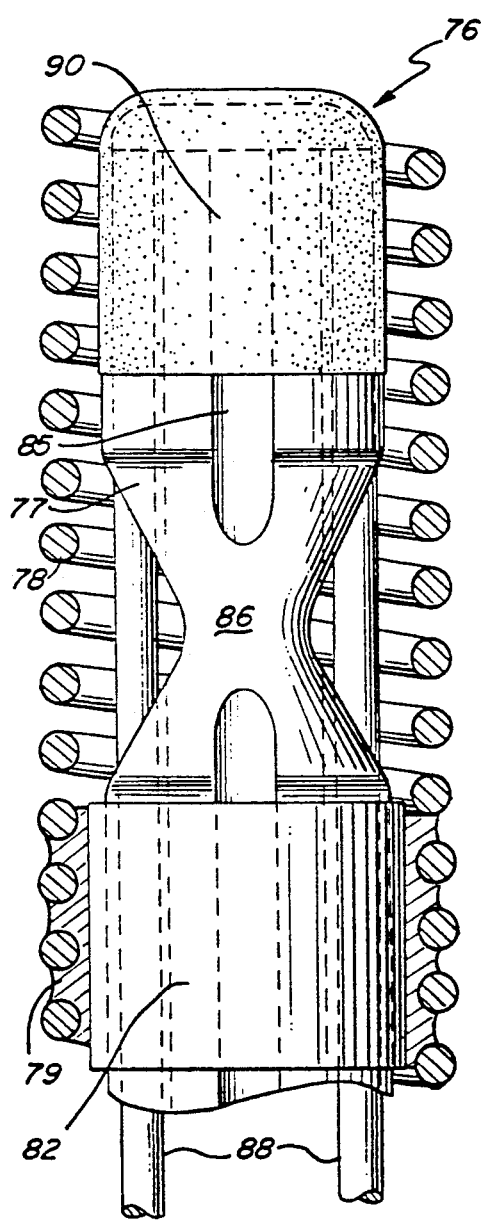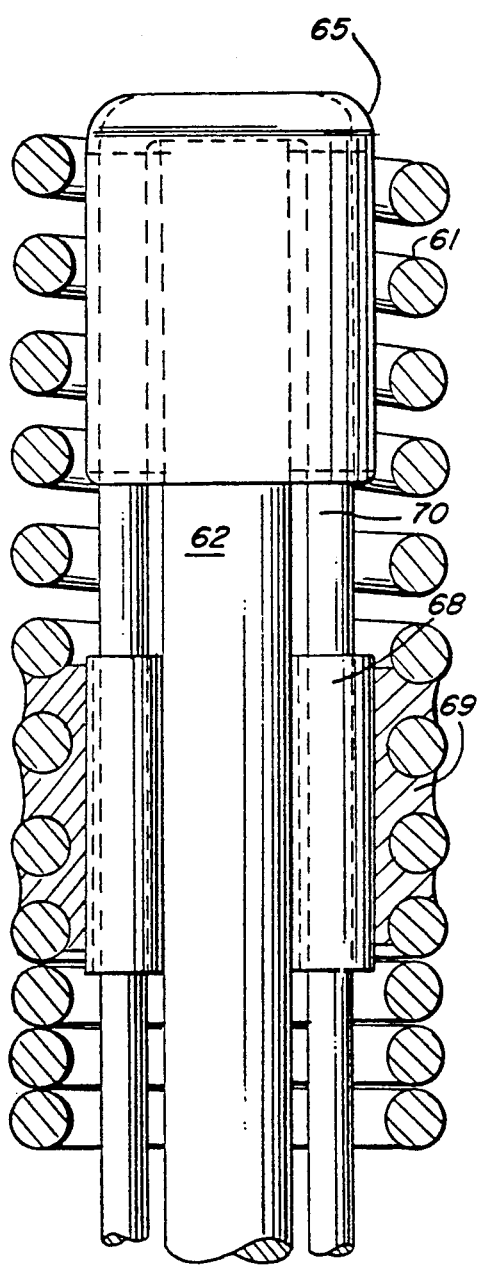

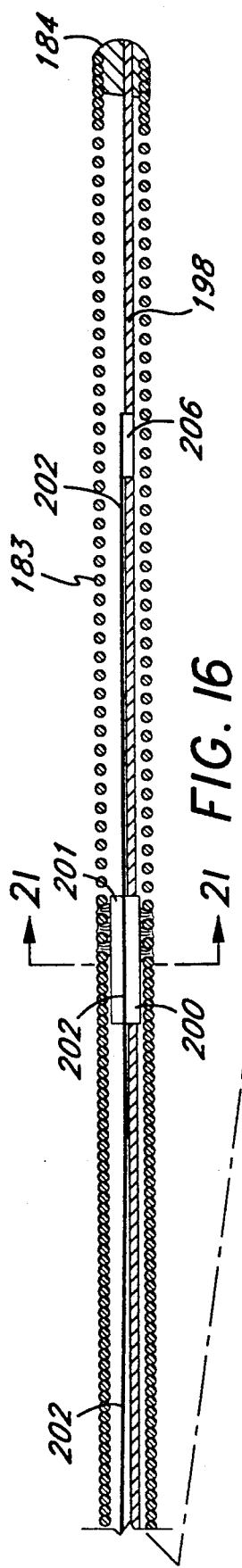
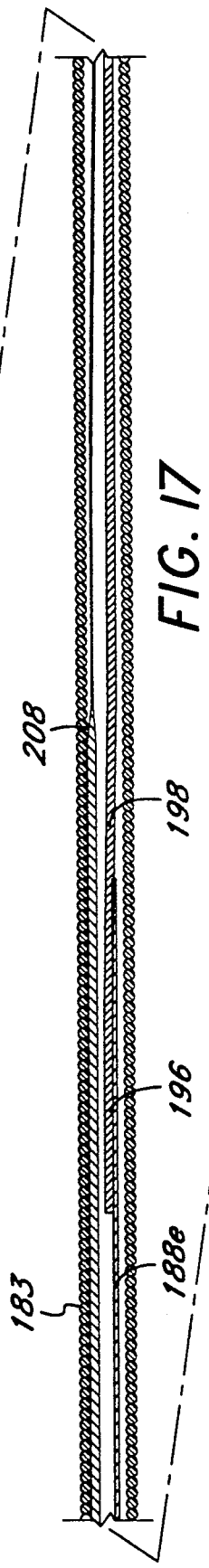
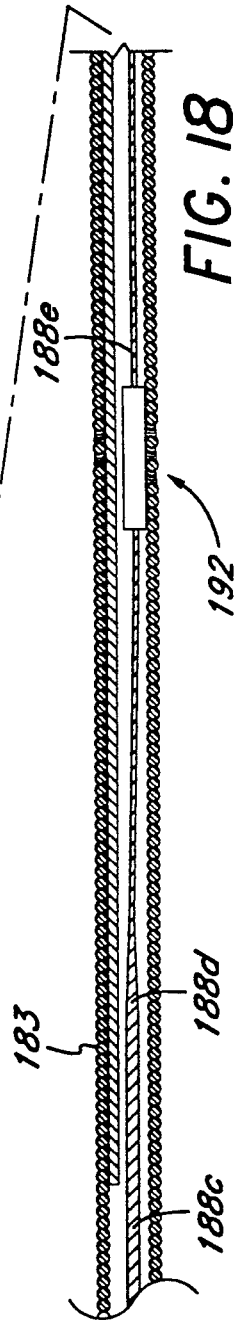

STEERABLE MEDICAL DEVICE

BACKGROUND OF THE INVENTION

This is a division of Ser. No. 865,357 filed Apr. 8, 1992 now U.S. Pat. No. 5,203,772 which is a Continuation-In-Part of application Ser. No. 583,819, filed Sep. 17, 1990, now U.S. Pat. No. 5,108,368 inventors Julius G. Hammerslag and Gary R. Hammerslag, entitled "Steerable Medical Device"; which is a Continuation-In-Part of application Ser. No. 461,049, filed Jan. 4, 1990, now U.S. Pat. No. 4,998,916; which is a Continuation-In-Part of application Ser. No. 295,124, filed Jan. 9, 1989, now U.S. Pat. No. 4,921,482.

The present invention relates to steering devices such as may be used with catheters, cannulae, guidewires and the like. More particularly, the present invention relates to catheters and guidewires that are steerable through body lumen or cavities and positionable within or aimable at obstructions, organs or tissue within the body from a position external to the body.

Medical catheters generally comprise elongate tube-like members which may be inserted into the body, either percutaneously or via a body orifice, for any of a wide variety of diagnostic and therapeutic purposes. Such medical applications frequently require use of a catheter having the ability to negotiate twists and turns, particularly with regard to certain cardiovascular applications.

One such application, "Percutaneous Transluminal coronary Angioplasty" (balloon angioplasty), requires manipulation of a catheter from a position outside the patient's body through extended portions of the patient's arterial system to the stenotic site for the purpose of alleviating the obstruction by inflating a balloon. This particular procedure has been performed with increasing frequency over the past years in preference to open heart bypass surgery, when possible.

In a typical angioplasty procedure, a guidewire is transluminally inserted into the brachial or the femoral artery, to be positioned within the stenotic region and followed by a balloon catheter. The cardiologist usually prebends the distal tip of the guidewire before insertion and then rotates (or torques) the wire once it has reached a branch artery to enable the guidewire to enter the branch. If the angle of the bend has to be adjusted, the guidewire must be removed, re-bent and reinserted, sometimes several times. Particular difficulty is encountered with prebending where an artery branches at one angle, and then sub-branches at a different angle. This procedure is attended by the risk of significant trauma to the arterial lining, and, in many cases, the obstruction cannot be reached at all with the guidewire and catheter.

Coronary arteries are tortuous, have many sub-branches and often the obstruction is either located where the diameter of the artery is small or, by its very presence, the obstruction leaves only a very small opening through which a guidewire and/or catheter can be passed. Consequently, the cardiologist often finds it very difficult to maneuver the guidewire or catheter, which are typically several feet long, from the proximal end.

Steering the prebent guidewire is further complicated by the fact that branches project at all different radial angles, thus necessitating rotation of the guidewire to the appropriate degree to enter the desired arterial branch. However, rotation of the distal end of the wire typically lags behind rotation of the proximal, control end, so that precise rotational control is not possible. Also, friction in the arteries can cause the distal end to rotate in a jerky fashion which can traumatize the vascular intima.

In another application, Transluminal Laser Catheter Angioplasty (laser angioplasty), the delivery of laser energy from an external source to an intraluminal site to remove plaque or thrombus obstructions in vessels is accomplished by providing a waveguide such as a fiber optic bundle within a catheter. The nature of laser angioplasty requires an even greater ability to precisely manipulate the catheter, to control and aim the laser light at the specific plaques or thrombi to be removed.

A variety of attempts have been made in the past to provide catheters which are steerable from the proximal end to enable the catheter to be aimed or advanced through non-linear body cavities. For example, U.S. Pat. No. 4,723,936 to Buchbinder, et al. discloses a balloon catheter, which is said to be steerable from the proximal end. The catheter is provided with a deflection wire going along the entire length of the catheter, which may be axially displaced to cause deflection. However, the tip of the catheter can be bent in one direction only, and the entire catheter must be rotated or torqued to be guided. A further disadvantage of this device is the inability to effectively straighten the catheter once it has been bent. Any ability of the Buchbinder catheter depends upon the axial compression of the steering wire therein. In addition, the design requires a relatively large diameter deflection wire, which precludes extremely thin diameter catheters, such as those preferred for use for laser or balloon angioplasty applications.

U.S. Pat. No. 3,470,876 to Barchilon discloses a catheter device having a central lumen extending therethrough, and four tensioning cords extending along an inner wall of the catheter. The '876 patent specifically recites that catheters may be produced in accordance with the Barchilon design having diameters of 0.125 to 2 inches, and are suited for applications such as within the duodenal bulb or ascending colon. These diameters are unsuited for use as a guidewire in coronary angioplasty, which typically requires diameters in the area of as small as from about 0.014 to 0.018 inches.

In the context of coronary angioplasty applications, the prior art generally suffers from disadvantages such as limited steerability and excessive external diameters. Limited catheter tip steerability results in greater time spent in the body and significantly elevated risk of trauma both to the vascular intima and to the patient in general. Multiple insertions of guidewires or catheters may lead to thrombosis, as a result of coagulation commencing along a guidewire surface. Additionally, precise directional control in laser angioplasty is of the utmost importance to assure accurate aiming of the laser beam to ablate the attendant plaque. However, the only prior art catheters having multi-directional steerability are typically greatly in excess of practical angioplasty catheter diameters.

In addition to limited steerability, the prior art guidewires, such as those disclosed by Buchbinder and in U.S. Pat. No. 4,719,924 to Crittenden, rely upon the spring tension of the guidewire coil (and the resilience of the distal end of the deflection wire, in the case of Buchbinder) to return the guidewire to the straight, unbent position. However, as important as deflecting the wire to enter a branch artery is straightening the wire after the branch is negotiated. Any ability to straighten in the prior art devices described above results from the spring tension or other structure in the distal end of the wire, which structures also compromise the desired floppiness of the guidewire tip.

Thus, there remains a need for a small diameter steering device, which may be readily adapted for use in the construction of either guidewires or catheters, and which is especially suited for procedures such as balloon or laser angioplasty. Preferably, the steering device is constructed in a manner which permits a diameter as small as that of existing dilatation catheters or guidewires used in angioplasty applications. The steering device additionally permits controlled lateral deflection of the distal tip.

SUMMARY OF THE INVENTION

There is provided in accordance with one aspect of the present invention a steerable device for insertion into a body cavity and controlled negotiation of branches and turns therein. The steerable device comprises an elongate flexible housing having a proximal end and a distal end and at least one lumen extending axially therethrough. A steering element is secured within the lumen and adapted to displace the distal end of the housing in a lateral direction.

At least one deflection wire is axially movably disposed within the lumen of the flexible housing, and extends from a distal point of attachment with respect to the steering element, throughout the length of the flexible housing to the proximal end thereof. Axial movement of the deflection wire in a proximal direction cooperates with the relatively fixed functional length of the steering element to produce a lateral force, thereby displacing the axis of a portion of the housing in a lateral direction.

Preferably, the proximal end of the functional region of the steering element is secured within the lumen to substantially prevent axial motion with respect to the tubular body. In one embodiment, the steering element is secured within the lumen by soldering.

Preferably, the steerable device further comprises a wire guide for axially slidably receiving the deflection wire, proximal to the point of attachment between the deflection wire and the steering element. A wire guide can conveniently be secured to both the interior wall of the elongate tubular body, and to the proximal end of the steering element.

In a preferred embodiment, the steerable device further comprises a means for transmitting rotational torque between the flexible housing and the deflection wire. The preferred torque transmitting means for use herein comprises complementary surface structures on the deflection wire and the interior of the tubular body, which permit axial reciprocal motion of the deflection wire within the tubular body, but substantially prevent rotation of the deflection wire with respect to the tubular body.

In accordance with a further aspect of the present invention, there is provided a steerable implement comprising an elongate flexible housing having proximal and distal ends and a central lumen extending therebetween. A steering region on the distal end of the housing is flexible in a lateral direction. An axially extending steering element is secured within the steering region of the housing and adapted to displace the steering region of the housing in the lateral direction.

At least one deflection wire is provided, having proximal and distal ends and extending along the housing. A distal portion of the wire is secured with respect to the steering element. A control is further provided at the proximal end of the housing for engaging the proximal end of the deflection wire to enable the deflection wire to be displaced axially in relation to the housing. The axis of at least a portion of the steering element is displaced laterally in response to axial displacement of the deflection wire, thereby causing the distal end of the housing to bend out of the line of the housing longitudinal axis.

Preferably, the steering element is secured with respect to the housing at a point within about 2 cm of the distal end of the housing to form a fulcrum. The elongate flexible housing is relatively axially noncompressable on the proximal side of the fulcrum. The axially noncompressable portion of the housing preferably comprises solid wall tubing and/or spring coil.

In a spring coil embodiment, the spring coil extends distally past the fulcrum and beyond the distal end of the steering element. The portion of the spring coil disposed distally of the fulcrum is loosely wound, so that adjacent windings of spring coil are not normally in contact with one another.

Preferably, the fulcrum comprises a tubular wire guide which is secured both to the interior of the elongate flexible housing, and to the steering element. Preferably, at least one torque transmitter is provided for transmitting rotation between the deflection wire and the tubular housing.

In accordance with a further aspect of the present invention, there is provided a torque transmitter for transmitting rotational torque between an elongate tubular guidewire or catheter housing and a core wire extending axially therethrough, said core wire of the type adapted for axial reciprocal movement with respect to the housing. The torque transmitter comprises a first torque transmitting surface on the core wire and a complementary second torque transmitting surface on the housing, so that engagement of the first and second transmitting surfaces transmits rotational movement between the core wire and the housing.

Preferably, the first torque transmitting surface on the core wire comprises a generally planer surface lying on an axis which is generally parallel to the -longitudinal axis of the core wire.

The second torque transmitting surface preferably comprises a region of reduced interior cross-sectional area of the lumen extending through the elongate tubular housing.

In an alternate embodiment of the torque transmitter in accordance with the present invention, the core wire is provided with a length of relatively flattened ribbon like torque transmission region. The torque transmission ribbon area extends through the lumen in a torque transmitter tube secured to the interior wall of the elongate housing. The lumen of the torque transmitter tube is provided with a noncircular interior cross-sectional configuration, such as oval or other flattened configuration to substantially prevent rotation of the ribbon within the torque transmitter tube.

In accordance with a further aspect of the present invention, there is provided a steerable device for percutaneous transluminal insertion into the coronary or peripheral vascular systems, and controlled negotiation of branches and turns therein. The device comprises an elongate support structure having a proximal and a distal end for transmitting axial force from the proximal end of the support structure to the distal end thereof. Transmission of axial force is accomplished principally by the non axially collapsible properties of the elongate support structure.

A steering element extends distally from the distal end of the support structure, thereby providing a fulcrum at the intersection of the support structure and the steering element. A core wire extends generally parallel to the support structure and is secured to the steering element at a point of attachment which is distal from the fulcrum. Axial movement of the core wire in a proximal direction relative to the support structure causes a lateral deflection of the steering element.

Preferably, the tubular body extends distally beyond the fulcrum to surround the steering element. Preferably, the fulcrum is disposed within about 10 mm from the distal end of the steerable device, and, more preferably, the fulcrum is disposed within about 6 mm from the distal end of the steerable device.

Further features and advantages of the present invention will be apparent from the detailed description of preferred embodiments which follows, when considered together with the attached drawings and claims.

BRIEF DESCRIPTION OF THE DRAWINGS

FIG. 4 is a partial sectional perspective view of a steerable laser angioplasty catheter according to the present invention.

FIG. 5 is a further embodiment of the steerable guidewire of the present invention.

FIG. 10 is a simplified front elevational view of the device shown in FIG. 8, following application of an anchor cap.

FIG. 11 is a simplified front elevational view of the device shown in FIG. 7, following application of an anchor cap.

FIGS. 16, 17 and 18 show an enlarged view of the guidewire illustrated in FIG. 15.

DETAILED DESCRIPTION OF PREFERRED EMBODIMENTS

Figure 1:
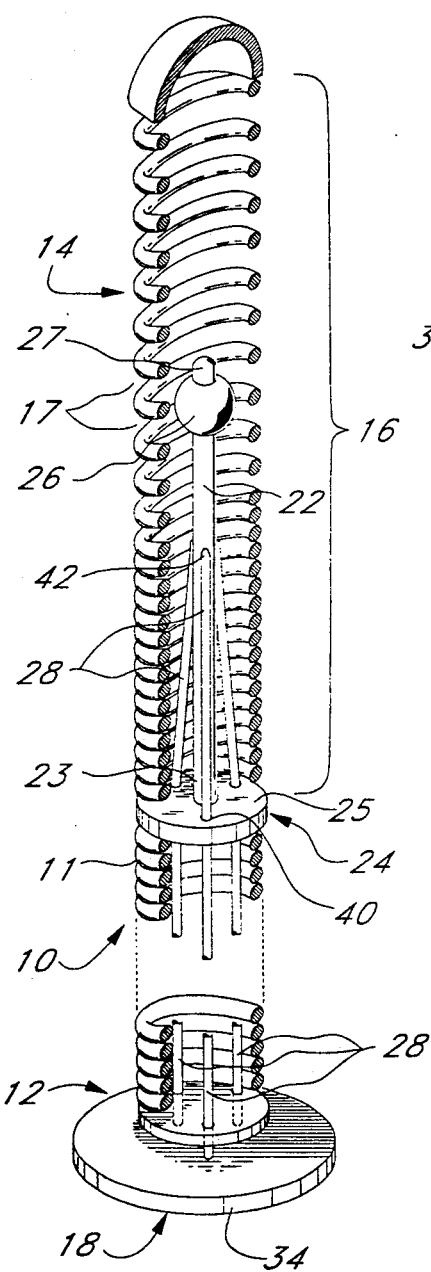
FIG. 1 is a partial sectional perspective view of a steerable guidewire according to the present invention, with the outer tubular casing removed.

Referring to FIG. 1, there is disclosed an elongate flexible implement 10, having a tubular body 11 with a proximal end 12 and a distal end 14. The distal end 14 comprises a steering region 16, and the proximal end 12 is provided with a control 18 for steering the implement 10, which may be, for example, a steerable guidewire or catheter. Although the steering device of the present invention will generally be described herein as incorporated into an angioplasty guidewire, it is to be understood that one skilled in the art will be able to readily adapt the steering device to other medical and nonmedical applications.

The body 11 of steerable implement 10 may be any desired length from inches to many feet depending upon the intended application. In an embodiment useful as an angioplasty guidewire or catheter, the body 11 will typically be several feet long, and will preferably be about 135–180 cm, as is typical of existing angioplasty catheters and guidewires respectively. However, any suitable length may be used. Typically, the proximal most 120 to 150 cm of the body 11 is hypotube, as is well known in the art, and the distal 30 cm comprises a metal coil.

The body 11 may be constructed in any of a variety of ways known in the art, such as by tightly winding a coil of metal wire, or extrusion of a relatively flexible biocompatible polymer such as polyethylene. Wound guidewires preferably comprise a high tensile strength wire of a resilient, non-corrosive metal such as stainless steel or platinum, and may have a circular cross section with a diameter of from about 0.001 to 0.020 in. The wire may alternatively have a rectangular cross section of from about 0.001 to 0.020 inches by from about 0.001 to 0.040 inches, or other variations known in the art. Construction materials and techniques for manufacturing wire wound guidewires are well known in the art, and a typical 180 cm teflon coated 0.014 inch or 0.016 inch diameter non-steerable guidewire may be obtained from U.S. Catheter, Inc., a division of C. R. Bard, Inc., located in Billerica, Mass., U.S.A.

The external diameter of wire wound guidewires will of course be a function of the intended application. The wire wound coronary angioplasty guidewires incorporating the steering device of the present invention are preferably wound to have an external diameter in the range of from about 0.014 inches to about 0.018 inches. In steerable catheter applications, the diameter of the catheter can be varied to optimize the diameter of a central working channel as desired, while still maintaining a sufficiently small exterior diameter for the intended application. Steerable balloon angioplasty catheters incorporating the present invention will typically have an exterior diameter in the range of from about 0.020 inches to about 0.041 inches or larger as permitted by location of the lesion.

Preferably, the exterior surface of the wound coil type guidewire shaft 10 is provided with an elastic, biocompatible coating or sheath to provide a smooth outer surface. Suitable coatings can be formed by dipping, spraying or wrapping and heat curing operations as are known in the art. Alternatively, heat shrinkable tubing can provide a suitable outer sheath. A coating material should be selected which will permit sufficient flexing of the body 11 without cracking, will minimize sliding friction of the implement 10 during insertion and removal, and is substantially chemically inert in the in vivo vascular environment. A variety of suitable materials are known, including, for example, polytetrafluoroethylene, urethane or polyethylene.

The body 11 of flexible implement 10 typically terminates at its distal end 14 in a closed tip 20. Numerous guidewire and catheter tip constructions are known in the art and need not be detailed extensively herein. Typically, the tip 20 is formed by a rounded braze or solder joint, which may also serve to secure the distal ends of the deflection wires. As a safety feature, to facilitate complete removal of fragments of a broken guidewire, the deflection wires can extend distally beyond their point of attachment to the ribbon or post, to function as a safety wire, or a separate safety wire may be secured at one end to the inside of the tip 20, and at the other end to the post 22 or support 24. Alternatively, the tip 20 is constructed of a resilient polymeric material such as silicone or urethane which will minimize trauma to the vascular intima, as will be appreciated by one of skill in the art.

Disposed intermediate the tip 20 and body 11 of a flexible implement 10 in accordance with the present invention is a floppy but controllable steering region 16. Steering region 16 is constructed in a manner that facilitates lateral displacement of the tip 20 relative to the axis of the body 11, through physical design and/or choice of flexible construction materials.

For example, in a typical angioplasty guidewire or catheter, where the flexible body 11 comprises a metal wire coil, the revolutions of wire per unit of axial distance along the body is reduced in the steering region 16 relative to body 11 to provide a looser wound coil having space 17 between adjacent wire loops, as illustrated in FIGS. 1-6. Thus, referring to FIG. 2, it can be seen that lateral deflection of steering region 16 to the left may involve both an axial compression of adjacent wire loops on the inside surface 36 of the bend, and an axial separation of the adjacent wire loops on the outside surface 38 of the bend.

Alternative designs or materials can be employed, provided that the catheter exhibits sufficient lateral flexibility. In general, the steering region 16 may be made from a variety of suitable metal or plastic coils or flexible sleeves. Materials opaque to X-rays, such as platinum, gold, tungsten, tantalum or the like, may be advantageously incorporated therein, to act as a fluoroscopic marker to aid in visualization.

In accordance with the "post" embodiment of the steering mechanism of the present invention, a steering post 22 is provided, extending in a generally axial direction within the steering region 16 of flexible body 11. Preferably, the steering post 22 is disposed coaxially within the central lumen of steering region 16 when the steering region 16 and body 11 are linearly aligned, such as when at rest. See FIG. 1. As will be described, the steering post 22 is secured in the steering region 16 in a manner that substantially prevents axial displacement thereof yet permits lateral deflection of the axis of the steering post 22 away from the axis of body 11.

Post 22 preferably comprises a resilient shaft which may be molded or extruded from any of a variety of materials, such as nylon, and may have a cross-sectional dimension of from about 0.002 inches up to about 0.012 inches for use in a typical steerable angioplasty guidewire embodiment. Alternatively, a variety of resilient or springy metals in the form of wire can also be used to form post 22, such as phosphor bronze, spring steel, Nitinol, or other resilient metal. In general, it is desirable to select a material which will permit some degree of bending and return to its original shape, and will resist axial compression under the forces typically applied in the intended use of the steerable implement 10.

The length of steering post 22 will, of course, be dependant upon the length of the steering region 16. In a typical steerable guidewire for angioplasty applications, the entire steering region 16 will be on the order of from about 0.040 to about 1.0 inches and preferably from about 0.120 to about 0.150 inches long, and the steering post 22 may be from one-quarter to two-thirds that length. Although steering post 22 may extend distally all the way to the distal tip 20 of the steerable implement 10, it is preferred to limit the length to the proximal one-half or one-third of the axial length of steering region 16 to minimize rigidity in the steering region 16 yet permit sufficient steerability thereof.

For example, in a typical angioplasty guidewire the distal end 27 of steering post 22 will be spaced apart from the interior surface of tip 20 by a distance of from about one-tenth to one-half an inch or more, thus permitting the steering region 16 of the catheter shaft to be as floppy as desired. However, in an embodiment where the distal portion of a fiber optics bundle or flexible tube for defining a working channel additionally functions as the steering post 22, the post 22 will extend all the way to the distal tip 20 and be exposed to the outside by way of an opening therethrough. See, for example, FIG. 4.

In a preferred embodiment, steering post 22 is further provided with a bead or enlarged region 26 to optimize transmission of lateral force from the steering post 22 to the wall of steering region 16. For this purpose, bead 26 is most effectively located at or near the distal end of steering post 22. Bead 26 may be formed by dipping or coating techniques, or may be a preformed member having an opening therein for sliding over the end of steering post 22. Alternatively, post 22 can be molded or milled to provide a bead 26 integrally formed thereon. Bead 26 is preferably substantially circular in a cross section perpendicular to the axis of post 22, and the external diameter of the bead 26 is only slightly less than the interior diameter of the steering region 16 so that maximum lateral motion of the steering post 22 is transmitted to the steering region 16, but bead 26 also remains only in slidable contact with the interior surface thereof.

The proximal end 23 of the steering post 22 is mounted to or in pivotable contact with a radial support 24, in a manner which permits pivoting of the steering post 22 throughout a full 360° range of motion about the axis of body 11. The post may also be molded or milled as an integral part of disk 24. The support 24 comprises any means by which the deflection wires 28 are displaced radially outwardly from the axis of the tubular body 11, such as by the thickness of the post 22 or other structure including the plate embodiment illustrated in FIGS. 1-3.

Referring to FIG. 1, the support 24 of the illustrated embodiment comprises a circular disk 25 located within the tubular body 11 of the steerable implement 10, preferably located near the distal end thereof. The disk 25 is axially secured within the tubular body 11 to provide a stationary radial support for at least one deflection wire 28, and pivotable mount for steering post 22. Disk 25 may be attached, for example, by friction fit between adjacent turns of coiled spring wire. Steering post 22 preferably is attached to or in contact with the disk 25 in a manner which permits it to swivel from 90 degrees to close to 0 degrees, relative to the lateral plane of disk 25.

The disk 25 may be made of stainless steel or any of a variety of other suitable materials such as other metals or plastic polymers which will provide a sufficiently axially rigid seat for the proximal end 23 of steering post 22. Disk 25 may be formed by stamping from sheet stock and drilling, injection molding, or other techniques well known in the art. Preferably, a central depression or orifice is provided thereon, for providing an axial seat for steering post 22. The diameter of disk 25 can vary, however, it will typically be no greater than, but may approximate the outside diameter of the steerable implement 10. Diameters from about 0.14 to 0.050 inches may preferably be used in the construction of cardiac angioplasty catheters.

Lateral deflection of the steering post 22 away from the axis of body 11 is accomplished by proximal axial displacement of any of a plurality of deflection wires 28 extending proximally throughout the length of flexible body 11. Although only a single deflection wire 28 or two deflection wires can be used, preferably three or four deflection wires 28 are employed in the "post" embodiment to provide a full 360° range of notion of the steering region 16 about the axis of the body 11, as will become apparent. Only a single deflection wire 28 will be described in detail herein.

The distal end of deflection wire 28 is secured such as by adhesives (or brazing or soldering, etc.) to the steering post 22 at the distal end thereof, or at a variety of other locations along the length of post 22. By "attached" or "secured" to the post and similar language herein, it is to be understood that the deflection wire 28 is mechanically linked to the post 22 but need not necessarily be directly secured thereto. For example, the deflection wire 28 could be secured to an annular flange or ring surrounding the post or other structure which may be convenient from a manufacturing standpoint to provide a sufficiently secure linkage to accomplish the intended steering function. Alternatively, an eye on the end of the deflection wire can surround the post 22 and rest against a stop formed by a milled shoulder or adhesive, or other means of attachment as will be apparent to one of skill in the art.

In one embodiment, the deflection wire 28 preferably extends radially outwardly from the point of attachment to the steering post 22 to the support 24. For this purpose, the support 24 is preferably provided with a notch or orifice 40 for each deflection wire 28 to extend through, said orifice 40 spaced radially outwardly from the axis of the tubular body 11 by a first distance. The distal end of each deflection wire 28 is secured to the steering post 22 at a point radially displaced from the axis of the steering post 22 by a second distance, and the first distance is preferably greater than the second distance to maximize the lateral component of force. The second distance preferably approaches zero; however, it will inherently include the radius of the steering post 22 where the deflection wire 28 is secured intermediate the two ends thereof.

In the preferred embodiment of the present invention, four deflection wires 28 are provided, each passing through an orifice 40 in support 24 spaced at angles of approximately 90° apart from each other along the plane of the support 24. In a three deflection wire embodiment, as illustrated in FIG. 1, each orifice 40 is separated from each adjacent orifice by an angle of approximately 120°.

The deflection wires may be made of stainless steel, nylon or any other suitable material which provides sufficient tensile strength and flexibility. Preferably, the deflection wires are braided from multiple strands, as is detailed below. The diameter of the wires can range from 0.001 to 0.005 inches or more, and suitability of particular sizes or materials can be readily determined by experimentation.

Figure 2:
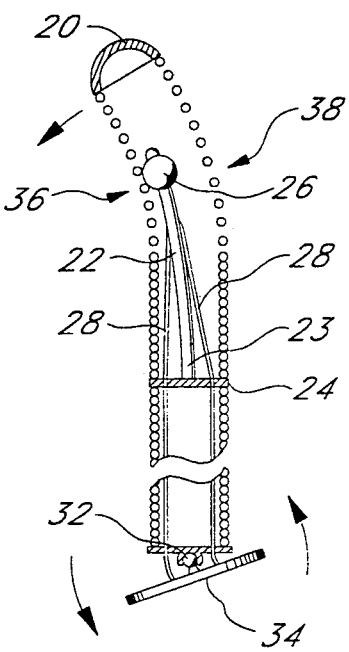
FIG. 2 is an elevational sectional view of the guidewire of FIG. 1, illustrated in a first deflected position.
Figure 3:
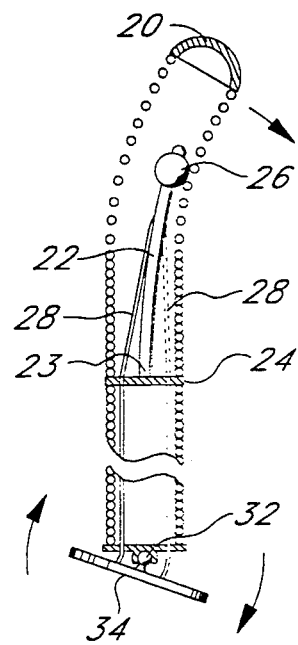
FIG. 3 is an elevational sectional view of the guidewire of FIG. 1, illustrated in a second deflected position.
Figure 6:
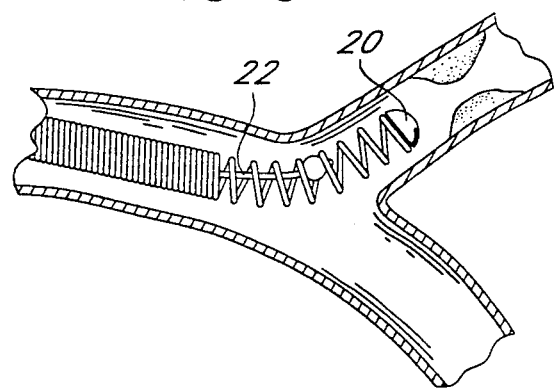
FIG. 6 is a schematic view of the guidewire of FIG. 1, illustrated as negotiating an arterial branch point and approaching an arterial stenosis.

A control device 18 for steering the catheter is shown schematically in FIGS. 1-3. The control device 18 is preferably provided at its center with a pivotable mount 32 to permit it to be tipped throughout a full 360° range of motion. In the illustrated embodiment, control 18 comprises a circular plate 34 secured to proximal end 12 of flexible shaft 10 by way of pivotable mount 32. Deflection wires 28 are spaced equally radially outwardly from the pivotable center of the control device and at equal angular distances around the plate 34. Deflecting plate 34 from a plane normal to the axis of shaft 10 transmits force via one or more deflection wires 28, a component of which is resolved into a lateral force to deflect the catheter tip toward or away from the longitudinal axis of catheter. Selective tipping of the deflection plate 34 results in rotation of the catheter tip to any desired orientation.

A variety of alternative control devices can be envisioned for use with the steerable implement of the present invention. For example, a "joy stick" type device comprising a single lever which can be displaced to any position throughout a nearly hemispherical range of motion might be used. As a further alternative, a portion of the proximal end 12 of tubular body 11 is enlarged to a cross section of a half inch or larger to facilitate grip. The enlarged section is provided with a plurality of axially slidable switches, one corresponding to each deflection wire 28. Manipulation of the switches by the thumb or forefinger will obtain the desired deflection of steering region 16. As will be appreciated by one of skill in the art, any control device will preferably be provided with a stop to prevent bending of the post 22 or steering region 16 past its elastic limit.

A variety of factors impact the amount of the lateral force component exerted on steering post 22 by axial, proximal displacement of any of deflection wires 28. For example, as orifice 40 is moved further in a radially outward direction, the lateral force component will increase. Lateral displacement of orifice 40, however, is constrained by the maximum diameter that the steerable implement can have for an intended application.

Alternatively, shortening the axial distance from the support 24 to the point of attachment 42 of the deflection wire 28 to the steering post 22 increases the angle between the axis of post 22 and deflection wire 28, thereby increasing the lateral component of force. For this reason, support 24 is typically within one or two inches, and preferably less than one inch, from the distal tip 20 of an angioplasty catheter or guidewire embodiment of the invention.

A further alternative is illustrated in FIG. 5. In this embodiment, a fulcrum 44 is provided at a point intermediate the radial support 24 and point of attachment 42 for maintaining the deflection wire 28 concave in a radial inward direction. The fulcrum 44 may conveniently comprise a substantially radially symmetrical member such as a sphere or toroid, which can also function to limit proximal axial movement of steering post 22 through a central opening in support 24. In this embodiment, the point of attachment of deflection wires 28 may be to the fulcrum 44 instead of directly to the steering post 22.

In accordance with a further aspect of the present invention, there is provided a steerable medical implement for use in percutaneous transluminal laser angioplasty applications. Referring to FIG. 4, there is disclosed an elongate flexible implement 45 comprising at its distal end a floppy steering region 46. As described with previous embodiments, enhanced flexibility may be imparted to steering region 46 by providing spacing 47 between adjacent loops of wound wire 48.

A radial support means 49 is disposed at the proximal end of steering region 46, which may comprise a circular plate 50 or other structure for displacing deflection wires 52 radially outwardly from the axis of implement 45.

A waveguide such as a fiber optic bundle 54 extends the entire length of the implement 45, for directing laser light from a source (not illustrated) disposed at the proximal end of the implement 45, to a point of application within a coronary artery at the distal tip 56 of the implement 45. For this purpose, the optical pathway 54 extends throughout the length of steering region 46 and traverses tip 56 by way of an opening 58 therein.

Each of the deflection wires 52 is secured at its distal end to the fiber optic bundle 54 at a point intermediate radial support 49 and distal tip 56. Preferably, as has been previously described, the point of attachment of deflection wires 52 to the fiber optic bundle 54 is less than half the distance and preferably is within one-third of the distance between the radial support 49 and distal tip 56, in order to optimize the lateral component of force.

Thus, utilizing a control device as previously described, a laser angioplasty catheter incorporating the present invention permits the controlled direction of a beam of light transmitted through fiber bundle 54 at any desired point within a full 360° circle on a plane normal to the axis of the implement 45.

As is well known in the fiber optics art, numerous functions can be accomplished through a waveguide such as fiber bundle 54. For example, substantially parallel but discrete bundles of fiber optics can be secured adjacent one another within the fiber bundle 54 to permit a plurality of discrete light transmitting channels. Alternatively, a plurality of concentric optical pathways can be provided as is well known in the art.

A plurality of discrete optical pathways may advantageously be used to perform a variety of functions. For example, a first optical pathway might be utilized to permit visualization of the stenotic site or other surface to be treated. A separate optical pathway may be utilized to transmit light for illuminating the site. Yet a third optical pathway might be utilized to transmit the laser light. These and other aspects of the fiber optics and laser light source are well known to those skilled in the fiber optics art.

A variety of additional functions may be performed through use of the additional interior space within the housing of steerable implement 45. For example, in a preferred embodiment, an aspiration duct may be provided near the distal end of the implement 45, for suctioning debris or gases which may be generated as a result of the action of the laser. Alternatively, in place of a waveguide 54, a flexible tube may be incorporated into the steering device of the present invention, thereby providing a working channel to receive additional implements therethrough.

Figure 7:
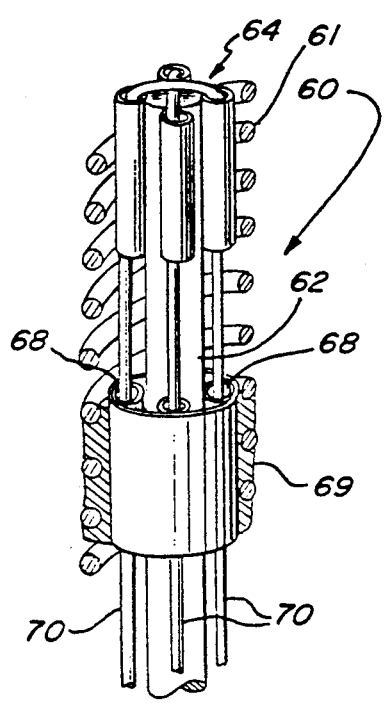
FIG. 7 is an elevational perspective view of a further embodiment of a steering device according to the present invention.

Referring to FIG. 7, there is disclosed a further embodiment of the steering device in accordance with the present invention. The steerable device illustrated in FIG. 7 can be incorporated into a guidewire, or directly into a catheter, such as a balloon dilation catheter, or other elongate implement for which steerability is desired. It is to be understood that while certain preferred dimensions and construction materials will be recited in the discussion of the present embodiment, these illustrate a single angioplasty guidewire embodiment only and in no way limit the scope of the present invention.

The steering device 60 preferably is incorporated into a steerable guidewire, of the type made from an elongate flexible hypotube and tubular spring coil 61 having a central lumen extending therethrough. The spring coil 61 may be further provided with an outer sheath or coating, as are known in the art, or the spring coil may, by itself, serve as the outer wall of the guidewire. As is well known in the art, the proximal end of the spring coil 61 is made up of a plurality of adjacent loops of wire, which may in turn be connected to a solid walled tube such as a length of hypodermic needle stock. Typically, a 150 cm length of hypotube, having a nominal 0.0135 inch outside diameter and 0.007 inch inside diameter will be used for this purpose.

Lateral flexibility of the spring coil 61 at a distal steering region can be enhanced by providing a spacing between adjacent loops of the spring coil. These features are illustrated in FIGS. 1–6 of a previous embodiment of the present invention, and need no further discussion here. Alternatively, the adjacent loops of wire in the steering region can be in contact with one another, i.e., no axial spacing, when the steering region is in an orientation co-linear with the axis of the adjacent guidewire.

Extending axially within the steering region of the spring coil 61 is a central post 62. Post 62 is preferably made from a flexible polymeric extrusion, or from a metal or metal alloy such as Nitinol, although any of a wide variety of materials can be incorporated into the post 62 of the present invention. Most preferably, he post 62 comprises a nylon rod having a substantially circular cross-sectional area and a diameter of about 0.004 inches.

The distal end 64 of post 62 preferably is disposed at or near the distal end of the spring coil 61. For example, the distal end 64 in one embodiment terminates proximally of the guidewire tip (not illustrated), similarly to the embodiment illustrated in FIG. 1. Alternatively, the distal end 64 is in contact with the guidewire tip, which can be molded or machined integrally with the post 62 or secured thereto such as by known biocompatible adhesives. In either embodiment, the distal end of the spring coil 61 is provided with any of the known atraumatic tips conventional in the angioplasty arts, such as those formed by molding or dipping or brazing processes.

The post 62 can extend in a distal direction beyond the distal ends of wire guides 72 and for a predetermined length. This can be one way of causing the steering region in operation to form an "elbow" bend, which is believed clinically desirable. In addition, the portion of post 62 disposed between the end of wire guide 72 and the guidewire tip can function as a safety wire for securing the guidewire tip against in vivo detachment.

By "elbow" bend, it is meant that the bend in the guidewire occurs at a relatively discrete position displaced proximally from the distal end of the guidewire. This enables a short length of floppy guidewire at the distal end to facilitate negotiation of the artery with minimal trauma to the vascular intima.

The length of the floppy tip beyond the more rigid steering region of the guidewire can be varied, depending upon a number of considerations which will be apparent to one of skill in the art, including the diameter of the vessels expected to be traversed. In one specific construction of the embodiment of FIGS. 7 and 11, for example, the relative dimensions are as follows. Length of each of guide 68 and anchor 72: about 0.010 inches. Axial distance between guide 68 and anchor 72: about 0.006 inches. Distance between end of anchor 72 and distal tip of guidewire: about 0.140 inches. Diameter of control post 62: about 0.004 inches. Diameter of spring wire of guidewire body: about 0.002 inches. Outside diameter of assembled guidewire: about 0.014 inches. In another specific embodiment, the length of the guides is about 0.060 inches, the length of the anchors is about 0.010 inches, the gap between the guides and anchors is about 0.070 inches, and the distance from the top of the guide to the distal end of the guidewire is about 0.140 inches.

The post 62 extends in a proximal direction through the spring coil 61 as far as may be desired for a given application, as will be understood by one of skill in the art. For example, the central post 62 may extend proximally only as far as the proximal wire guide 68, or further in a proximal direction to impart greater rigidity to the spring coil 61 than would otherwise be present.

The post 62 should at some point along its length be secured against axial movement in the proximal direction relative to the spring coil 61. From a manufacturing standpoint, it has been found convenient to secure the proximal wire guides 68 both to the post 62 and to the interior surface of spring coil 61 for this purpose as will be discussed. However, the post 62 can also be secured to the coil 61 at other locations, such as at the proximal end of an axially elongated post 62.

A plurality of proximal wire guides 68 are provided, one for guiding each of a plurality of deflection wires 70. Preferably, four proximal wire guides 68 are provided, equally spaced about the periphery of the central post 62. As will be apparent to one of skill in the art, three wire guides 68 spaced equidistant around the periphery of central post 62 will also allow complete 360° steerability about the axis of the guidewire. However, the use of four deflection wires 70 is preferred. Similarly, the guidewire can be constructed having only two or even a single deflection wire and proximal wire guide 68, with a commensurate reduction in the annular range of motion over which the guidewire may be steered.

A plurality of deflection wires 70 extend axially throughout the length of the spring (;oil 61, each through a unique proximal wire guide 68 to the: distal end 64 of post 62. Preferably, the distal end 64 of post 62 is also provided with a plurality of distal wire guides 72, which can also function as wire anchors, corresponding to each deflection wire 70.

In accordance with the preferred "post" embodiment of the present invention, four deflection wires 70 are utilized, each deflection wire 70 having a unique proximal wire guide 68 and distal wire guide 72. Each of the deflection wires 70 may be secured to the distal end of the post in any of a variety of manners, which will be apparent to one of skill in the art, such as by mechanical anchors, adhesives or thermal or chemical welding, or metal fastening techniques such as brazing or soldering, depending upon construction materials.

Mechanical anchoring or welding of the distal end of deflection wire 70 may be difficult to accomplish while providing sufficient strength to allow repeated steering maneuvers of the steering device 60 without separation of the distal end of deflection wire 70 from the distal end 64 of post 62. Thus, although the preferred embodiment is effectively provided with four deflection wires 70, they are actually two continuous deflection wires which loop across the distal end 64 of the post 62. A first deflection wire 70 extends distally through distal wire guide 72, continuously around or over the distal end 64 of central post 62 and back proximally through the opposing wire guide 72 and continuing on towards the proximal end of the instrument. Alternatively, the distal ends of the deflection wires are twisted or braided together, and extend as a safety wire up to the distal tip of the guidewire. In this manner, all four ends of the two continuous wires terminate at the proximal end of the guidewire where they connect to a control device permitting selective axial reciprocating motion thereof.

In accordance with one preferred embodiment of the present invention, proximal wire guide 68 is in the form of an elongate tubular body for receiving the corresponding deflection wire 70 therethrough. The tubular wire guide 68 preferably is comprised of a material which can be readily adhered to the central post 62, and preferably also can be adhered to the adjacent loops of spring coil 61. Polyimide tubing, such as that manufactured by Polymicro Technologies, Inc. in Phoenix, Ariz., having an axial length of approximately 0.010 inches and an inside diameter of slightly greater than 0.0015 inches, preferably about 0.002 inches, has been found particularly suitable for this purpose, and can be readily adhered to a nylon post 62 using a suitable epoxy adhesive, such as that marketed under the name Ecobond by Emmerson Cuming of Canton, Mass. In accordance with another embodiment of the invention, the distal wire guide 72 is approximately 0.010 inches along and the proximal wire guide 68 is about 0.030 inches long. Alternatively, metal tubing, such as solid wall tubing or wire wound tubing can be conveniently soldered or brazed to a metal post.

Figure 8:
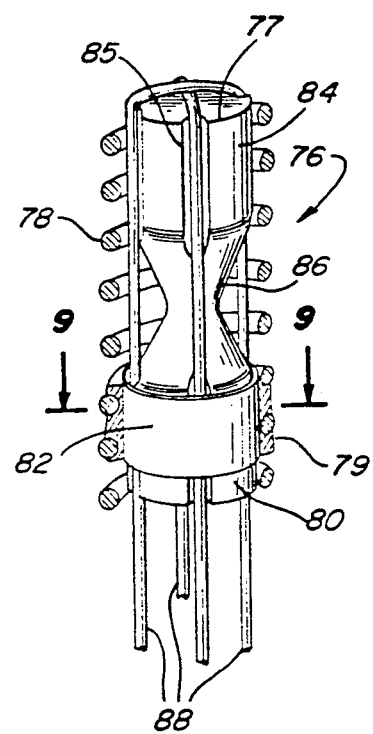
FIG. 8 is an elevational perspective view of still a further embodiment of the present invention.

The length of the tube is generally less important than the diameter, and the diameter must be sufficient that a deflection wire extending therethrough is capable of reciprocal motion with sufficiently low friction that steering may be accomplished. The wall thickness of the tube will directly affect the minimum diameter of the assembled steerable guidewire, and is thus preferably minimized. For the polyimide tube disclosed above, the wall thickness is preferably as low as about 0.0003 inches. As illustrated in FIG. 8, the proximal wire guide 68 is conveniently affixed to the spring coil 61 by applying an epoxy 69 thereto. the proximal wire guide 68, and preferably through a distal wire guide 72. Deflection wire 70 is a fine wire of a diameter sufficient to provide enough tensile strength to allow steering of the guidewire without breaking, but small enough to permit construction of guidewires suitable for angioplasty applications. Preferably, a stainless steel wire is used, and diameters as low as about 0.0015 inches have been found functionally sufficient. However, a variety of other metals or polymers may be used, and the minimum appropriate diameter for any given material can be readily determined by one of skill in the art.

Distal wire guide 72 is in the preferred embodiment a similar construction to proximal wire guide 68. Thus, distal wire guides 72 are formed by a plurality of elongate tubular guides adhered to the central post 62 for receiving the corresponding deflection wire 70 therethrough. Alternatively, the distal wire guide 72 can simply be a groove over the distal end 64 of post 62, or a bore hole extending transversely through the center of central post 62.

Assembly of the steering device of the present invention may be accomplished in a variety of ways which will be understood by one of skill in the art, with many of the assembly steps being performed under microscopic vision. The proximal wire guide 68 and distal wire guide 72, when used, are preferably secured to the central post 62 by applying an adhesive thereto such as by dabbing with a 0.0015 inch diameter wire as an applicator. A first deflection wire 70 is threaded in a distal direction through corresponding proximal wire guide 68, through distal wire guide 72, then back in a proximal direction through the corresponding wire guides on the opposite side of post 62 and drawn through to the proximal end of the instrument. This assembly procedure is repeated for a second deflection wire. With the deflection wires 70 in place, the entire distal end 64 of post 62 is dipped in or dabbed with an epoxy or other biologically compatible material to form a cap 65 to secure each of the deflection wires 70 against axial movement relative to the control post 62. See FIG. 11.

The entire assembly of post 62 wire guides and deflection wires is thereafter inserted distal end first into the proximal end of a standard spring coil 61 and advanced until the proximal wire guide 68 is approximately axially adjacent the beginning of the distal flexible steering region on the spring coil 61. An epoxy or other biocompatible adhesive 69 is thereafter applied between the adjacent loops of spring coil 61 to secure the proximal wire guides 68 to the spring coil 61, thereby preventing axial movement of the post 62 relative to the spring coil 61. It has been found that polyimide tubing can be epoxied to the adjacent spring coil 61 using a 0.002 inch wire or other applicator tip under microscopic vision. However, care must be taken that the epoxy does not flow into contact with the deflection wire 70, in which case the deflection wire 70 would be unable to slide axially within the proximal wire guide 68.

Figure 9:
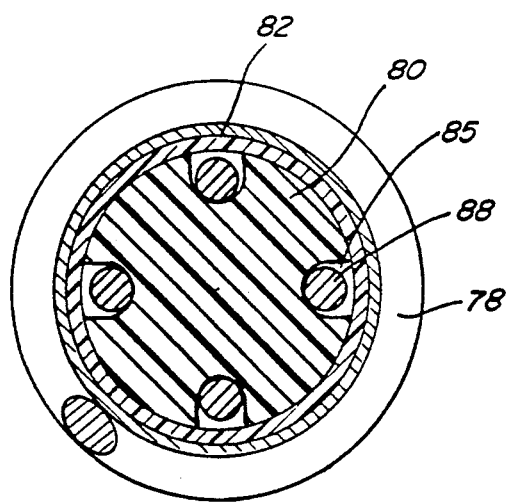
FIG. 9 is a cross-sectional view along the line 9—9 of the device of FIG. 8.

Referring to FIGS. 8-10, there is disclosed a further embodiment of the steering device in accordance with the present invention. The steering device 76 comprises a main body 77 having a proximal wire guide 80, a wire anchor 84 and a pivot region 86. Preferably, the wire guide 80, pivot 86 and anchor 84 are integrally formed from a single extrusion or molded part.

In accordance with a preferred embodiment of the invention, the main body 77 has a maximum diameter of as small as about 0.009 inches or smaller, and is substantially circular in outer cross-sectional configuration, except for a plurality of axially extending channels 85 for receiving guidewires 88 therethrough. Each of the channels 85 preferably has a depth of approximately 0.002 inches, so that 0.0015-inch diameter stainless steel wire can slidably extend therethrough. Channels 85 can conveniently be formed in the extrusion process as axial recesses of the type illustrated in FIGS. 8-10, or by providing parallel sets of radially outwardly extending flanges which extend axially to create a channel 85 therebetween.

Pivot 86 may be formed in any of a variety of ways, which will be apparent to one of skill in the art, and which will depend upon the construction material utilized. For example, in the case of a thermoplastic polymeric extrusion, the pivot region 86 preferably comprises a radially inwardly extending annular depression, which may be formed by application of heat and pressure or by stretching following the extrusion process. Alternatively, the pivot region 86 can be provided by producing an annular recess through other operations such as by physically milling or cutting portions of the extrusion away, or, wire guide 80 and anchor 84 can be secured to a length of metal or polymeric wire, spaced axially apart to provide a flexible length of wire therebetween.

Preferably, the steering device 76 is provided with a deflection wire 88 at each of the four 90° positions around the periphery thereof. (See FIG. 9.) As has been previously discussed, this can be accomplished by providing four separate guidewires which are anchored at the distal end of the steering device 76. However, four deflection wires 88 are effectively provided by assembling the steering device 76 with two continuous deflection wires 88, which loop over the distal end of wire anchor 84 and extend back in a proximal direction as has been discussed.

In assembling the embodiment of the steering device 76 illustrated in FIGS. 8-10, the deflection wires 88 are preferably crossed over the distal end of an extruded main body 77, axially aligned with the free ends extending in the proximal direction. The distal end of the wire anchor 84 is thereafter dipped in or dabbed with an appropriate adhesive, such as an epoxy, to form a cap 90 for securing the deflection wires 88 to the wire anchor 84.

A tubular sleeve 82, such as a length of heat-shrink tubing, is thereafter passed over the distal end of wire anchor 84 and advanced proximally into alignment with the proximal wire guide 80 in a manner which captures each wire 88 within the respective channel 85. Upon application of heat, the annular sleeve 82 reduces in diameter to snugly adhere to the proximal wire guide 80. It has been found that the use of channels 81, having a depth of approximately 0.002 inches, leaves a sufficient tolerance after heat shrinking of sleeve 82 so that stainless steel wires having a diameter of approximately 0.0015 inches can freely axially move therethrough.

The steering assembly is thereafter inserted into a standard guidewire coil 78, and advanced until the proximal wire guide 80 is approximately aligned with the proximal end of the flexible steering region of the coil 78. The radial outside surface of the annular sleeve 82 may thereafter be secured to the adjacent coil loops of coil 78, such as by the application of an epoxy or other adhesive 79, as has previously been described.

As will be apparent to one of skill in the art, axial movement of any given deflection wire 88 in a proximal direction will cause the wire 88 to slide through the channel 81 in proximal wire guide 80, and, because the wire 88 is immovably secured to the wire anchor 84, pivot region 86 will flex to permit lateral displacement of wire anchor 84 in the direction of the wire 88 which has been proximally displaced. In this manner, as has been described, the steering device 76 permits selective lateral displacement of the distal tip in any direction, and restoration of the position of the distal end of the steering device back into axial alignment with the axis of the adjacent portion of the guidewire or catheter.

In a modified version (not illustrated) of the device illustrated in FIGS. 8–10, the pivot region 86 is deleted so that the assembled device has an anchor region 84 and a wire guide 80 axially spaced apart and secured to the coils of guidewire body 78. Thus, no post appears in this embodiment. In this embodiment, the deflection wires extend distally from the wire guide 80 toward the anchor 84 as before, but instead of extending substantially parallel to the axis of the steering device 76 as illustrated in FIGS. 8 and 10, each deflection wire crosses the axis of the steering device to the opposite side thereof. Thus, for example, one deflection wire 70 extends through wire guide 80 at the 90° position, then distally at an incline relative to the axis of the steering device to the 180° position on the anchor 84. The wire 70 thereafter in the preferred embodiment loops around the distal end of anchor 84 and extends proximally through the channel 85 at the 90° position thereof. Wire 70 thereafter extends diagonally across the axis of the steering device, through the wire guide 80 at the 180° position, and proximally to the steering control.

As a further alternative, the distal ends of the deflection wires (which may be the midpoint of a long, doubled back wire as previously discussed) are brazed directly to the wire coils of the guidewire body. A brazed joint is most conveniently accomplished on the outside surface of the guidewire body, and the deflection wires preferably extend radially outwardly between adjacent loops on the guidewire body for this purpose. In the case of two deflection wires formed from a single length of wire looping around the steering region of the guidewire, the deflection wire is conveniently looped around the outside of the guidewire body to provide a site for brazing. When a brazed joint is used, the distal wire anchor 84 can be deleted.

Figure 12:
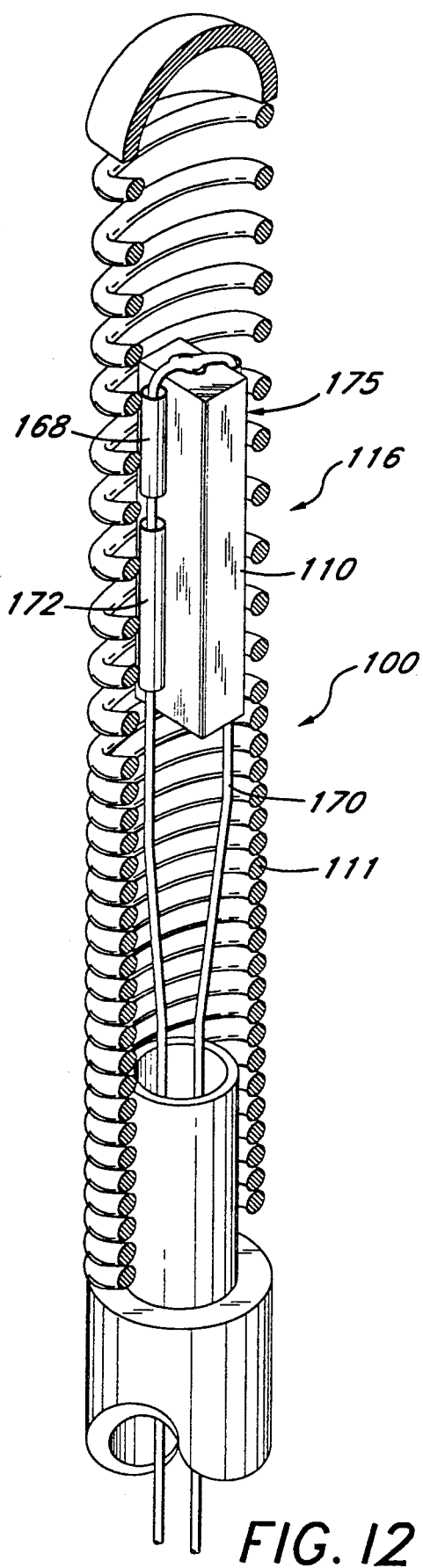
FIG. 12 is a partial sectional perspective view of a "ribbon" steering device according to the present invention, with the outer tubular casing removed.
Figure 13:
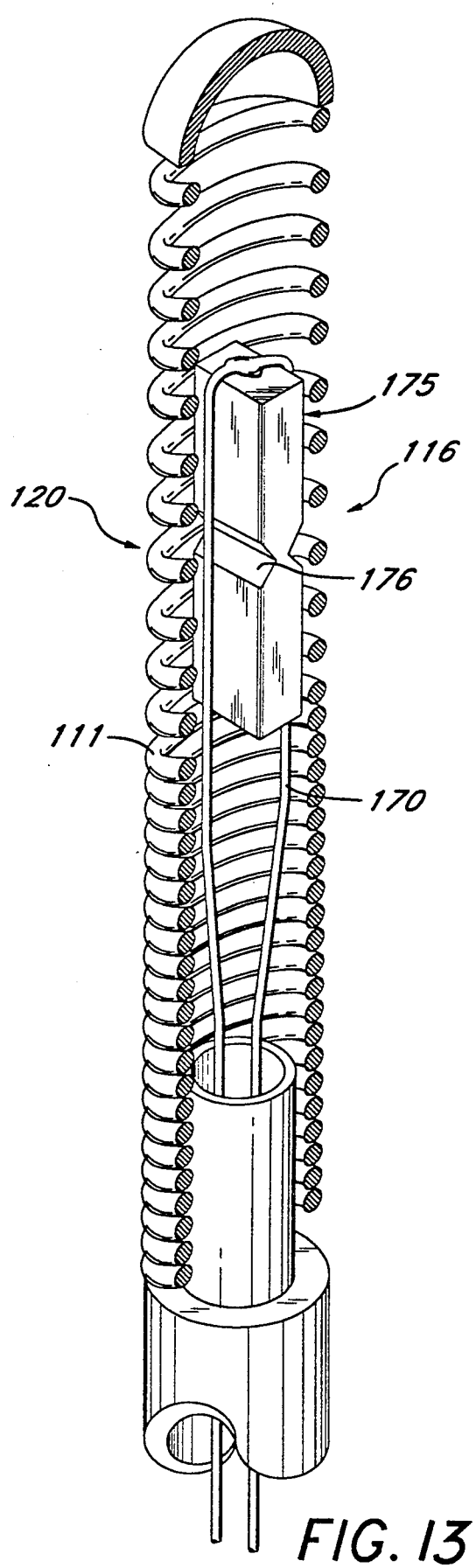
FIG. 13 is an elevational perspective view of a another embodiment of a "ribbon" steering device according to the present invention.
Figure 14:
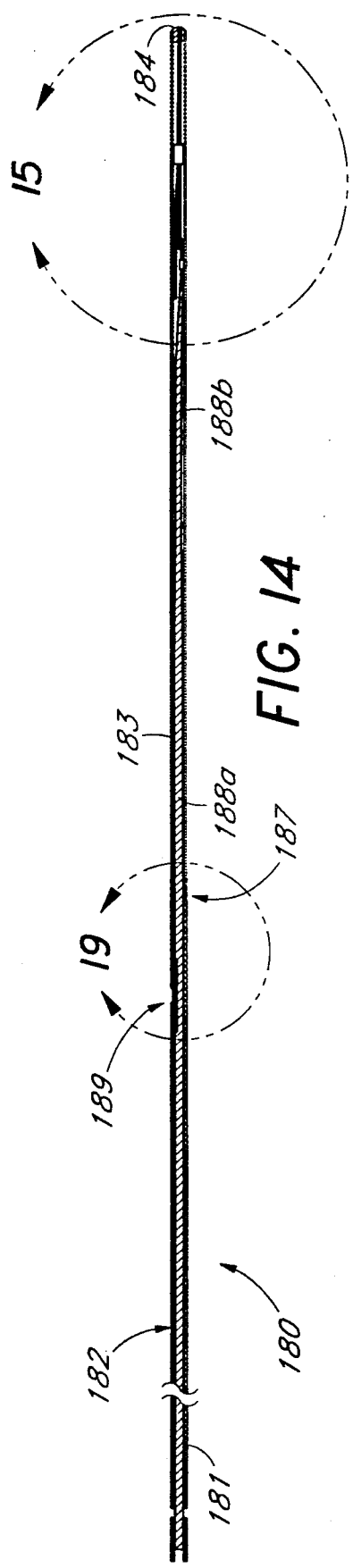
FIG. 14 is a side-elevational view of a guidewire incorporating a single deflection wire embodiment of the steering device in accordance with the present invention.
Figure 15:
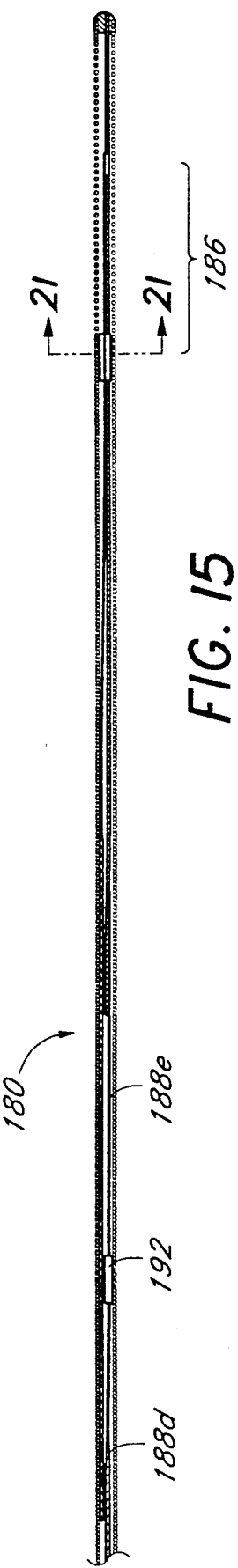
FIG. 15 is an enlargement of a distal portion of the guidewire illustrated in FIG. 14.

Referring now to FIGS. 12 and 13, there is shown in FIG. 12 a partial sectional perspective view of a two-wire "ribbon" type steering device 100 with the outer tubular casing removed. FIG. 13 shows a partial sectional perspective view of a another embodiment of a two-wire steering device 120 according to the present invention. The tubular outer body 111 of the steering devices 100, 120 can be similar to that of any of the various embodiments previously described.

In the steering devices 100, 120 shown, there is provided a flexible steering ribbon 110 disposed within the central lumen of the steering region 116 of the tubular outer body. As will be discussed, "flexible" can mean either a ribbon which can be physically bent or flexed in use, or a more rigid structure provided with a narrowing thereon or other type of pivot to form a hinge. In this embodiment, rather than complete 360° annular steerability about the axis of the guidewire, controlled steerability within a single plane is achieved. One improvement over the prior art is that the steering region of the device, once controllably bent, can be restraightened by applying a positive traction to at least One of the deflection wires.

The steering ribbon 110 may be molded, milled or extruded from any of ion or other plastic such as Nitinol, spring steel, nylon or other plastic materials. Preferably, the material will permit sufficient lateral flexibility while also exhibiting sufficient axial compressive strength to optimize transfer of axial force into lateral deflection. In another embodiment of the steering device 100, 120, the steering ribbon 110 may be replaced by two or more substantially parallel ribbons or wires. Ribbon 110 can be brazed or otherwise secured directly to the body 111, or indirectly through proximal wire guides, as illustrated in FIG. 12.

The ribbon 110 is preferably made from a shape-memory Nitinol alloy having a transition temperature of less than about 20° C. Nitinol al is a thermal-memory nickel-titanium metal alloy that is flexible and characterized by a high tensile strength, as well as a high endurance limit to stress fatigue. Nitinol has been found to be repeatedly deformable without apparent loss of resiliency at the site of deformation.

The preferred Nitinol transition temperature for the invention described herein is well below body temperature, such as 0° C. Those skilled in the art will appreciate that the transition temperature of the Nitinol family of alloys can be manipulated over a relatively wide range by altering the nickel-titanium ratio, by adding small amounts of other elements, and by varying deformation and annealing processes. While Nitinol alloys having a range of transition temperatures can be used, the transition temperature of the Nitinol alloy of this invention should be sufficiently lower than the surrounding ambient temperature to prevent transition from occurring during use. Nitinol can be obtained from Shape Memory Applications, Inc., Sunnyvale, Calif.

The steering ribbon 110, as shown, is preferably of substantially rectangular cross section but could also be of a variety of shapes including those that are substantially circular or ovoid. In general, any configuration which tends to promote the desired flexibility in a single plane may be used, although a circular cross section structure may also be used.

The narrower dimension of the approximately rectangular cross section illustrated in FIGS. 12 and 13 is preferably within the range of about 0.0005 to about 0.003 inches. The low end of the range represents about as narrow a dimension as the inventors believe will be functional, given the known materials. The upper end of the range is only really limited by the desired overall diameter of the instrument which, for example, may utilize a spring coil, body having an inside diameter of 0.010 inches and an outside diameter of 0.014 inches. In addition, increasing ribbon widths will tend to require increased force to bend the ribbon.

Similarly, the long side of the rectangular cross section is limited at its maximum by the available inside diameter of the outer flexible coil. In accordance with one preferred embodiment, the cross-sectional dimension of a rectangular ribbon for use in a guidewire is about 0.001±50% by 0.007±50% inches. Preferably, the ribbon 110 has substantially the same cross-sectional area throughout its length, except in the region of a hinge in an embodiment such as that illustrated in FIG. 13.

Flexibility across an arc of 180° or more in a single plane can also be facilitated by an appropriate pinching or narrowing of the ribbon 110. In the embodiment shown in FIG. 13, the hinge 175 is provided by an indentation 176 within the ribbon 110.

The hinge of FIG. 13 may be formed by molding, pinching, milling or stretching operations to form a narrowing having a greater propensity to bend than other portions of the ribbon 110. Preferably, the hinge is formed by pinching in a ribbon 110 having a rectangular cross section, however, any cross-sectional configuration may be used so long as flexibility in a single plane is encouraged and the ribbon 110 has sufficient rigidity and strength to withstand the forces applied in multiple flexings and straightenings needed in steering the body 111.

In the embodiment shown by FIG. 12, the flexible hinge region 175 is effectively provided by an axial space between tubular deflection wire guide 172 and anchor 168 which can be similar to the corresponding structures described in connection with the embodiment illustrated in FIG. 7. Preferably, there is one guide 172 and one anchor 168 on each side of the ribbon 110 for each of two deflection wires 170. The guides 172 and anchors 168 function to position the wires 70 axially along the steering ribbon as described in connection with FIG. 7 for securing the wires 70 to the steering post.

The exact length of the polyimide tubes preferably utilized as wire guides is not critical but the combined length of the tubing for guide 172 and anchor 168 should typically be less than the overall ribbon length. The length, diameter, construction and assembly of the guides 172 and anchors 168 will be readily understood by one of skill in the art by reference to the drawings and description above and in connection with FIG. 7. In one embodiment, the wire guide 172 is about 0.030 inches in length and the wire anchor 168 is about 0.010 inches in length.

The distance between the wire guide 172 and anchor 168 influences the ability of the ribbon to deform in response to axial displacement of the deflection wires. It is contemplated that a useful distance between coaxial wire guides and anchors is from about 0.010 to about 0.100 inches, with a preferred distance of from about 0.020 to about 0.090 inches, and a still more preferred distance of about 0.050 inches. Depending on the overall dimensions of the steering apparatus it is believed that a distance of up to 1 inch or more between guides 172 and anchors 168 is feasible. However, such an increase in distance between the guides and anchors would create a longer hinge region requiring thicker ribbon dimensions to counter the tendency of the increased length to buckle, and to provide flexibility comparable to the preferred embodiment. In addition, excessive length between the wire guide and wire anchor will tend to result in too gradual an arc during steering to negotiate relatively sharp arterial branches.

The ribbon of FIG. 12 can be coated with a substance to provide additional support to regions of the ribbon proximal and distal to the hinge. This support layer or coating may be applied during manufacture in a coextrusion process or, alternatively, the layer may be applied following or during ribbon manufacture as a dip or spray. Suitable coatings or support layer material include but are not limited to polyimide, nylon or cyanoacrylate. The coating can be applied over the entire ribbon surface or the coating can be applied to the distal and proximal ends leaving the hinge region uncoated. If the support layer or coating is applied over the entire ribbon surface, the coating over the hinge region can be subsequently removed in at least one location by scraping, grinding, cutting, melting or by laser. By providing the axial space 175 between guide 172 and anchor 168 that is at least partially uncoated, greater flexibility in the hinge region is achieved as compared with the proximal or distal sections of the ribbon.

The coating can be applied in a uniform thickness or it can be applied non-uniformly. The thickness of the coating is determined by the method of application as well as by physical constraints imparted by the dimensions of the apparatus. For example, the final width of the ribbon together with the tubing and deflecting wires need be less than the functional inner diameter of the flexible housing thus providing a limit to the coating thickness. The coating can be applied so that it is thicker on the proximal portion of the ribbon relative to the distal portion thereby minimizing ribbon movement relative to the housing at the proximal portion yet permitting movement of the ribbon relative to the housing at the distal portion of the ribbon. Conveniently, the coating can also function as the adhesive to secure the wire guides and wire anchors to the ribbon.

In the preferred embodiment, the deflection wires 170 are formed as a multi-filament complex. Alternatively, each deflection wire could consist of a single wire filament. The multi-wire filaments of the preferred embodiment are twisted or braided together to give about the same strength as a wire monofilament of the same overall diameter yet the multi-filament nature provides added flexibility. A range of from about 3–10 monofilament strands that are braided or entwined together are contemplated. Preferably, 7 strands of type 304 stainless steel each with a diameter of about 0.0005 inches are braided to provide an overall diameter of about 0.0015 inches. The seven strand multi-filament wire provides tensile strength on the order of 400,000–450,000 psi and is roughly equal in diameter to the single strand deflection wire previously described. Suitable wire strands can be obtained from Fort Wayne Metals Research Products Corp., Fort Wayne, Ind.

The multi-filament bundle or single strand deflection wire could have an overall diameter in the range 0.001 to 0.005 inches. The choice of final wire diameter is limited by the internal diameter of the wire housing that contains the ribbon, polyimide tubing and deflection wire as well as by the tensile strength required to translate an applied axial force into lateral deflection.

A lubricous coating is preferably applied to the surface of the deflection wire in order to facilitate smooth motion of the wire in the housing. Any of polyimide, silicone, polytetrafluoroethylene or nylon can be applied to the surface of the wires to facilitate smooth movement of the wire along the proximal end of the steering ribbon. In a preferred embodiment, polytetrafluoroethylene coated deflection wire is employed to permit even, continuous movement in response to an applied steering force. The wire can be coated by spray, dip, or other means known to one of skill in the art.

As discussed in connection with previous embodiments, at least one deflection wire 170 is secured with respect to the ribbon 110. In a preferred embodiment, there are two deflection wires 170, one on each of two opposing sides of the ribbon 110 with the distal most portions of the deflection wires (which may be the midpoint of a continuous, doubled back wire as previously discussed) secured with respect to the steering ribbon 110. Securing may be done by brazing, gluing, welding or soldering the wire directly to the top of the steering ribbon.

The deflection wires alternatively continue distally of the ribbon and meet at a centrally fixed location where they are twisted or coiled together. This joint may be additionally strengthened and affixed by soldering, brazing, or gluing the wires to the distal end of the ribbon 110. One or both of the wires preferably continues distally and is affixed to the catheter tip such as by soldering or brazing to provide a safety wire.

Torque is readily transmitted from the proximal control to the distal steering apparatus by either the use of hypodermic needle tubing or by triplex spring supplied by Microspring Company, Inc., Nowell, Mass. Like the deflection wire, the triplex spring guidewire could also be coated with a biocompatible lubricous coating. Such a coating could reduce friction between the guidewire and the vessel wall. Triplex spring provides the guidewire housing with sufficient rigidity such that force applied at the proximal end of the device is efficiently transferred to the distal steering ribbon.

The triplex spring should be closely coiled over the majority of the apparatus and preferably at least about ⅞ of the overall length of the device. The distal end of the apparatus is comprised of a small region of loose coiling that is bounded on either side by coiling having a rigidity that is greater than the loose coiling but less rigid than the triplex spring. Thus, the majority of the apparatus is formed from the triplex spring with the distal region, preferably one eight or less of the total length, made of coiling of intermediate rigidity, followed by flexible coiling and ending in coiling of intermediate rigidity. The steering ribbon is positioned at or near the proximal junction of the intermediate coiling and the looser coiling. Thus proximally applied force is translated to the steering ribbon and the looser coil within the steering region deflects laterally in response to ribbon deflection thereby providing a steering direction.

In use, the steering device 100 or 120 can be steered in either of two directly opposite steering directions by displacing one of the deflection wires 170. By axial displacement of either of the two deflection wires, a range of motion of the tip of the device is achieved along a semicircular arc within a plane lying on the longitudinal axis of the steering device 100, 120.

After the device is introduced into the vasculature or other branched system, and a branch or a turn is encountered, in order to enter the branch or turn, the device can be rotated (torqued) to align one of the two steering directions with the branch or turn to be entered. The device can be steered by axial displacement of one of the deflection wires. Advantageously, after the device has been steered toward one direction, the device can be easily straightened to some degree by displacing the deflection wire opposing the side toward which the device was steered. The device can then be further advanced through the vasculature.

Referring to FIGS. 14–23, there is disclosed a steerable guide wire 180 in accordance with a further embodiment of the present invention. Although disclosed in the context of a guidewire embodiment, the steering and torque transmission aspects of this embodiment of the present invention can be used in a variety of other implements, such as in a steerable balloon catheter or "balloon on a wire" design. Guide wire 180 generally comprises an elongate tubular body portion 182, and a distal tip 184. steering region 186 is disposed with in about 2 cm, and preferably within about 1 cm of the distal tip 184.

The body of steerable guide wire 180 may be any desired length from inches to many feet depending upon the intended application. In a typical angioplasty guide wire or catheter, the body will typically be several feet long, and preferably will be within the range from about 135 cm to 175 typical of existing angioplasty catheters and guide wires, respectively. Guide wires are typically somewhat longer than the corresponding catheter to facilitate catheter insertion and exchange as is well known in the art.

The proximal portion 181 of the tubular body 182 typically comprises hypodermic needle tubing, although other materials such as a spring coil or polymeric tube are also known for this Purpose. The distal portion of the tubular body preferably comprises a Metal coil. The proximal hypotube section is typically about 155 cm in length, and the distal metal coil section is typically about 30 cm in length. To facilitate visualization, either the distal most 2 cm or so of the spring coil, or the entire 30 cm of spring coil comprises platinum or other radiopaque material.

Preferably, the hypotube section 181 of the main body 182 in a guidewire or balloon on a wire embodiment for coronary vascular applications has an outside diameter of from about 0.013 to about 0.018 inches and an inside diameter of within the range of from about 0.008 to about 0.009 inches or larger. Preferably, the inside diameter is approximately 0.0085 inches. For peripheral vascular applications, the hypotube section 181 will typically have an external diameter on the order of from about 0.035 to about 0.040 inches. Suitable hypodermic needle stock is available from a variety of sources, such as the 304 stainless steel hypodermic stock available from MicroGroup, Inc., Medway, Mass., Popper and Sons Corp., New Hyde Park, N.Y., or Uniform Tubes, Inc., Collegeville, Pa.

Figure 19:
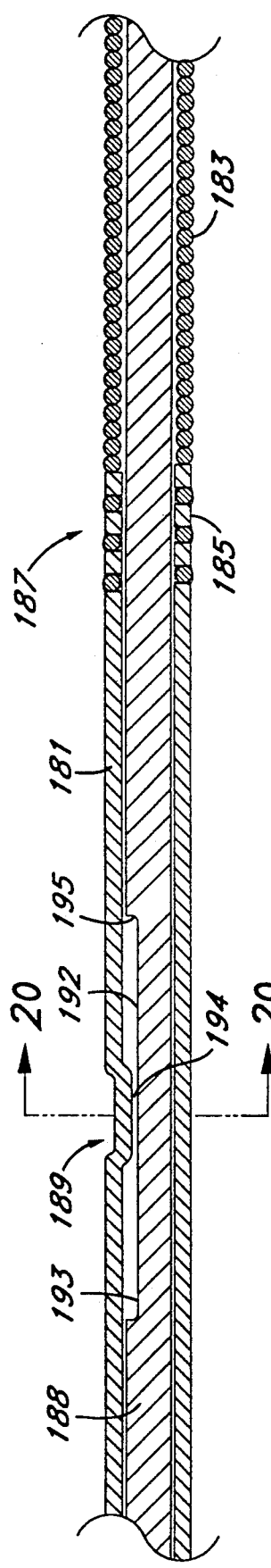
FIG. 19 is a side-elevational view of the region marked 19 in FIG. 14.
Figure 21:
FIG. 21 is an elevational cross-sectional view taken along the lines 21—21 in FIG. 15.

The proximal hypodermic needle stock section 181 and distal wire coil section 183 are merged at a transition section 187. Referring to FIG. 19, the transition from the hypodermic needle stock 181 to the spring coil 183 is preferably accomplished with a minimal or no change in either the inside diameter or the outside diameter of the body 182. In the illustrated embodiment, the distal end 185 of the hypodermic tube section 181 is provided with a helical channel such as by a wire electrical discharge machine (EDM) utilizing techniques which are known in the art. In general, the hypotube is fixtured in a servomotor controlled rotary indexer which accurately rotates the tube while the entire fixture is advanced at a controlled rate. The EDM machine is stationary and the wire is advanced into the hypotube wall to cut the spiral as the tube rotates and advances. See, for example, FIG. 22, illustrating the helical channel cut into the distal end 185 of the hypotube segment.

Figure 22:
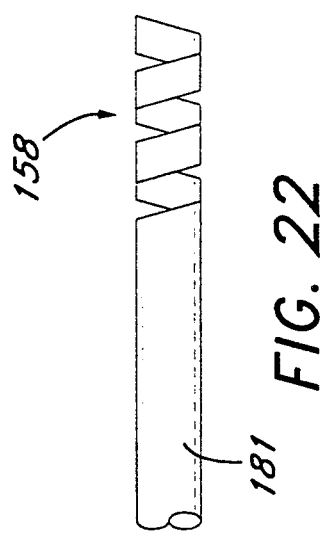
FIG. 22 illustrates a helical channel in the distal end of a hypotube segment, adapted to receive a spring coil.

Referring to FIG. 22, there is disclosed a helical channel having a channel width within the range of from about 0.0025 to about 0.0030 inches. The channel defines a helical ribbon having a width within the range of from about 0.0080 to about 0.0090 inches. The hypotube in the illustrated embodiment has an outside diameter of about 0.013 inches, and the helical channel was cut into the distal portion of a hypotube segment having an axial length of about 150.5 cm. Preferably, the hypotube is provided with at least 3 or 4 complete threads.

The proximal most windings of the coil 183 are threaded onto the helical channel, to provide a transition 187 having a mechanical interfit between the two adjacent sections. The transition 187 is strengthened by flowing solder or other suitable bonding material into the helical channels with the coil installed. Thereafter, the exterior may be polished to a smooth surface. However, any of a variety of other junctions between solid tubing stock and spring coil stock may be utilized, as may be known to or devised by persons skilled in the art.

The metal coil section 183 may be constructed in any of a variety of ways known in the art, such as by tightly winding a coil of a high tensile strength wire of a resilient, noncorrosive metal such as stainless steel or platinum. Typical wire for this purpose will have a circular cross-section with a diameter of from about 0.001 to about 0.005 inches. Alternatively, the wire may have a rectangular cross-section of from about 0.001 to about 0.020 inches by from about 0.001 to about 0.040 inches, or other variations known in the art. More preferably, the rectangular wire embodiment has cross sectional dimensions of from about 0.001 to about 0.004 by from about 0.004 to about 0.010 inches. The preferred coil for use in the present embodiment is a tightly wound stainless steel or platinum wire having a diameter of about 0.0025, to produce a coil having inside diameter of about 0.0085 inches and an outside diameter of about 0.0135 inches.

The distal portion of the metal coil section 183 comprises a steering region 186. See FIGS. 15 and 16. Preferably, the windings of the spring coil 183 distal to the wire guide 200 are separated slightly, to increase the relative flexibility of the steering region 186. "Loosely" wound coil sections may be produced in accordance with a variety of techniques well known in the art.

The steerability function of the guidewire in accordance with the present invention is optimized if the adjacent windings of spring coil 183 are "tightly wound" or in contact with each other proximally to wire guide 200. This resists axial compression and enables the wire guide 200 to function as the steering "platform" as has been described in previous embodiments. In this manner, and in view of the additional function of wire guide 200 of providing an axial anchor for steering ribbon 202, proximal motion of pull wire 188 produces a lateral component of force as the effective length of the pull wire segment between guide wire 200 and junction 206 is reduced compared to the fixed axial length of the steering ribbon 202 between wire guide 200 and junction 206.

That portion of the steering element between its point of attachment with respect to the coil 183 and its point of attachment to the pull wire thus functions in the same manner as the "post" and "ribbon" described in connection with previously described embodiments. Although the post in this embodiment is secured against axial movement by being secured to the wire guide 200, other means of attachment can be utilized to practice the present invention. For example, plate 50 illustrated in FIG. 4 or other structure which can be inserted between adjacent windings can be used. Alternatively, the steering ribbon 202 can be bonded directly to the interior of spring coil 183.

In view of the foregoing description of the steering mechanism of the present embodiment, which will be described in greater detail infra, two advantages of the designs disclosed herein can be seen. Initially, the length of the guidewire disposed between the "platform" formed in this embodiment by wire guide 200 secured to the spring coil 183 and the junction 206 directly affect the radius of the bend produced in the guidewire by axial displacement of pull wire 188.

For example, in an embodiment having an outer diameter of 0.014 and a distance from wire guide 200 to distal junction 206 of 0.100, the radius of the turn when bent to about a 90° angle is about 0.06. In general, desirable radii in a percutaneous coronary transluminal angioplasty application will be within the range of from about 0.020 to 0.180. However, individual cardiologists may develop a preference for a wire having a particular radius of curvature, which may be within or outside of the above recited range. In general, increasing the distance between the wire guide 200 and the distal junction 206 will enlarge the radius of curvature while decreasing the distance between the wire guide 200 and the distal junction 206 will reduce the radius of curvature. The precise distance required to produce a given radius can be readily determined through routine experimentation by one of skill in the art.

A second advantage of the designs disclosed herein is that the distance from the center of the bend to the distal tip 184 of the guidewire 180 can also be varied as desired. For example, in the embodiment illustrated herein, the distal junction 206 is displace proximally from the distal tip 184 of the steerable guidewire 180 by approximately 2 mm. This produces a "dogleg" bend, which, as previously described, is preferred by many cardiologist. By varying the relative location of the steering region 186 within the guidewire 180, the relative dimensions of the dogleg bend can be varied as will be appreciated by one of skill in the art.

Extending axially through the central lumen of the steerable guide wire 180 is a first pull wire segment 188. First pull wire segment 188 preferably comprises a solid wire made from a metal or polymer having good axial compressive strength and torque transmission characteristics. In the illustrated embodiment, first pull wire segment 188 comprises a stainless steel wire having a proximal portion 188a of circular cross-section, having a diameter of approximately 0.0075 inches. The outer diameter of pull wire 188 and inside diameter of hypotube section 181 may be varied within a relatively wide range as will be understood by one of skill in the art, as long as the pull wire segment 188 remains axially movable within hypotube section 181 without excess friction.

Figure 20:
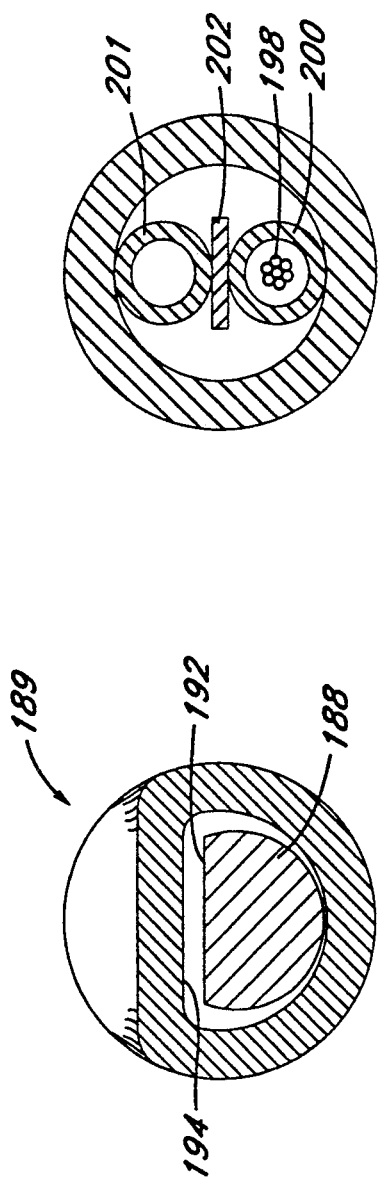
FIG. 20 is an elevational cross-sectional view through the lines 20—20 in FIG. 19.

Transmission of torque along the length of the guidewire 180 is optimized by inclusion of an optional torque transmitter 189 between the pull wire 188 and hypotube section 181. Referring to FIGS. 19 and 20, torque transmitter 189 comprises a flat 192 provided on the surface of pull wire 188 such as by milling or grinding. The flat 192 cooperates with a corresponding torque surface 194 on the hypotube 181. Torque surface 194 is preferably provided by crimping the hypotube to produce a flat or irregular wall section thereon.

The axial length of the flat 192 is preferably within the range from about 0.2 cm to about 0.5 cm, thereby producing a proximal shoulder 193 and a distal shoulder 195. The separation of the proximal shoulder 193 and distal shoulder 195 can, if desired, be utilized to limit the axial range of motion of the pull wire 188 within tubular body 182 as will be apparent to one of skill in the art. In general, the axial range of travel of the pull wire 188 within the guidewire body is about 0.200 inches or less for normal steerability. The depth of the flat 192 can vary considerably, but, in a preferred embodiment, is within the range of from about 0.0045 to about 0.0055 inches.

Alternatively, the flat section 192 can extend the entire length of first pull wire segment 188, or first pull wire segment 188 can comprise a rectangular wire throughout or other cross-sectional configuration susceptical to rotational interlocking such as by a torque surface 194. Preferably, however, at least the portion of the pull wire 188 that extends within the spring coil 183 is circular in cross section to minimize whipping.

In the illustrated embodiment, portion 188a of first pull wire segment 188 extends distally from a circular cross section of about 0.0075 inches at the torque transmitter 189 through one or a series of transition zones, to a reduced cross-sectional rectangular dimension of about 0.001 inches by about 0.003 inches at 188e. See FIG. 23. The cross sectional area reduction (continuous taper or steps) can extend over any of a variety of axial lengths, as will be apparent to one of skill in the art. The rate of taper has been found to affect the relative flexibility of the tip, and the present inventors prefer the taper to occur over an axial length of about 12 cm. Tapering can be smooth or stepped, and can be accomplished in any of a variety of manners, such as by grinding in a centerless grinder or an O.D. grinder. Flattening of distal portion 188e is then accomplished by compression between adjacent rollers or other technique depending upon the construction material.

Figure 23:
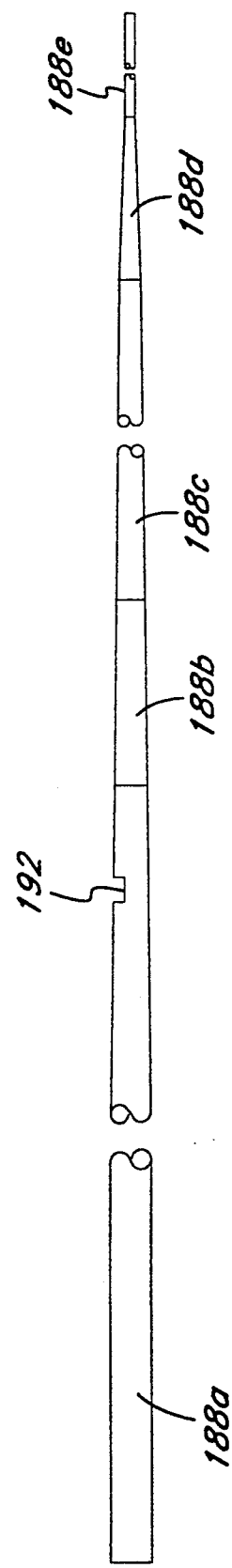
FIG. 23 illustrates one embodiment of a central core wire or deflection wire in accordance with one aspect of the present invention.

In the preferred embodiment, the cross sectional dimension of the pull wire 188 is reduced in the distal direction over a series of steps as illustrated in FIG. 23. Proximal portion 188a, in a preferred coronary artery embodiment, has a diameter of approximately 0.0075 inches. At about 13 cm from the distal end of segment 188e, a transition 188b reduces the diameter to 0.0060 inches at 188c. The axial length of the transition 188b is approximately 3.5 cm. The axial length of segment 188c is about 6.0 cm.

Thereafter, at about 3.5 cm from the distal end of section 188e, transition 188d begins. Transition 188d provides a taper over an axial length of about 3 cm to a segment 188e having a diameter of approximately 0.0025 inches. Prior to assembly of the steerable guidewire 180, the segment 188e is flattened between adjacent rollers to produce a rectangular ribbon having a thickness of about 0.0010 inches. The length of section 188e is thereafter trimmed to approximately 5 mm.

Referring to FIG. 18, a second torque transmitter 192 is disposed within the coil 183 distally of transition 188d for axially slidably receiving flattened region 188e of the first pull wire segment 188. Torque transmitter 192 preferably comprises a structure affixed to the interior wall of coil 183, having a configuration to rotationally engage the flattened region 188e of first pull wire segment 188. Preferably, torque transmitter 192 comprises a length of tubing which has been molded or compressed into a generally oval cross-sectional configuration for receiving flattened region 188e.

For this purpose, stainless steel hypotube stock having a 0.004 inch inside diameter and 0.007 inch outside diameter, and cut to a length of approximately 0.030 inches, is flattened in a die having stops to prevent complete collapse as will be understood by one of skill in the art. The resulting oval mini hypotube may be soldered to the adjacent windings of coil 183, to rotationally link the coil 183 with the flattened region 188e of first pull wire segment 188. Additional variations on torque transmitter 192 will be apparent to one of skill in the art in view of the present disclosure.

First pull wire segment 188e is connected to a second pull wire segment 198 at junction 196. Preferably, junction 196 comprises a length of overlap of the first pull wire segment 188e and second pull wire segment 198, which are connected such as by soldering. Although the foregoing design is preferred by the present inventors, the main pull wire 188 can alternatively extend throughout the length of the guidewire, without any joints or discontinuities.

Second pull wire segment 198 preferably comprises a flexible pull wire such as a multifilament stranded wire having an outside diameter of about 0.002 inches. Second pull wire segment 198 preferably extends all the way from junction 196 to the distal tip 184 where it is linked to the coil 183 and or tip 184 such as by soldering. That portion of segment 198 which extends between junction 206 and tip 184 functions as a safety wire.

In a multifilament embodiment, a range of from about 3 to about 10 monofilament strands are braided or entwined together to produce the second pull wire segment 198. Due to braiding geometry, 3 or 7 strands are generally used. Preferably, seven strands of type 304 stainless steel each having a diameter of about 0.0007 inches are braided to provide a pull wire having an overall diameter of about 0.002 inches as has been previously discussed.

Second pull wire segment 198 extends distally from junction 196 through a wire guide 200. Wire guide 200 preferably comprises a tubular body which is secured to both the windings of the coil 183 and to the steering ribbon 202. Preferably, the wire guide 200 has an inside diameter of about 0.0025 inches and an outside diameter of about 0.0035 inches, made from wire having a diameter of about 0.0005 inches. Suitable tubular wire guides can be produced by winding fine wire about a wire mandrel to produce a small coil. Stainless steel wire having a diameter of about 0.0023 inches has been found preferable for this purpose.

The wire guide 200 is preferably soldered to adjacent loops of wire coil 183. Although a variety of methods are known in the art for securing components of guide wires together, such as adhesives, thermal bonding, solvent bonding, brazing and the like, solder has been preferred by the present inventors. Thus, all of the components of the guide wire disclosed in this embodiment are preferably stainless steel or other solderable metal. Soldering, which can be conducted in the area of about 500° Fahrenheit is preferred over brazing, which requires higher temperatures in the neighborhood of about 1200° Fahrenheit. Brazing temperatures have appeared to the present inventors to induce fatigue and increase the likelihood of failure in the finished product.

Preferably, the wire guide 200 has an axial length of about 0.030 inches, although any of a variety of axial lengths can be utilized as will be apparent to one of skill in the art.

Steering ribbon 202 extends distally from wire guide 200 for about 0.1 inches, where it is affixed such as by soldering to the second pull wire segment 198 at distal junction 206. Steering ribbon 202 preferably also extends proximally from the wire guide 200 to regulate the flexibility of the steerable guide wire 180. In the illustrated embodiment, steering ribbon 202 extends proximally for a distance slightly in excess of about 2 cm. Approximately midway between the wire guide 200 and the proximal end of steering ribbon 202 is a transition 208 at which the outside dimensions of the steering ribbon are reduced from about 0.001 by 0.003 inches on the proximal side of transition 208 to about 0.0004 by 0.008 inches on the distal side of transition 208.

The wire guide 200 can be conveniently secured within coil 183 by separating the adjacent loops slightly and soldering the coil 183 directly to the wire guide coil 200. Alternatively, a spacer 201 formed from a second coil or wire can be adhered to the opposing side of steering ribbon 202 to provide additional bonding strength. Spacer 201 is similarly soldered or otherwise secured both to the interior of adjacent windings on coil 183 and to steering ribbon 202.

In one particular embodiment of a guide wire incorporating this aspect of the present invention, the distance from the distal tip 184 to the distal end of junction 206 was 2.3 mm. The length of junction 206 was approximately 0.015 inches. The distance from the proximal end of junction 206 to the distal end of wire guide 200 was approximately 0.100 inches. The axial length of wire guide 200 was about 0.030 inches. Thus, the distance from the distal tip 184 to the distal end of wire guide 200 was approximately 5.25 mm.

The distance from distal tip 184 to the transition 208 on steering ribbon 202 was approximately 13.30 mm. Transition section 208 was disposed approximately 1 mm to the distal side of the distal end of junction 196. The junction 196 comprised an overlap of flattened region 194 on first pull wire segment 188 and second pull wire segment 198 of approximately 2 mm. The overall distance from the distal end of torque transmitter 189 to the distal tip 184 was approximately 20.00 mm.

The foregoing dimensions may be varied considerably, depending on the intended use of steering devices incorporating the present invention, as will be readily understood by one of skill in the art.

It must be pointed out that the devices of the present invention can readily be modified by one of skill in the art to allow lateral displacement in only a single direction instead of two opposing directions. For example, the groove in a living hinge type device can be provided on only a single side of the steering ribbon, or other means for stopping or resisting flexing in one direction can be employed as will be readily apparent to one of skill in the art.

An advantage of the simplified steering devices 100, 120 of the present invention is that they can be operated in a manner similar to that employed on conventional steering devices for coronary angioplasty and other medical procedures. Thus, one skilled in the art of the prior art procedures could learn to manipulate the steering device of the present invention with little or no additional training.

Although this invention has been described in terms of certain preferred embodiments, other embodiments that are apparent to those of ordinary skill in the art are also within the scope of this invention. Accordingly, the scope of the invention is intended to be defined only by reference to the appended claims.

We claim:

1. A steerable device for transluminal insertion into a body cavity and controlled negotiation of branches and turns therein, said device comprising:

an elongate flexible housing having a proximal end and a distal end and at least one lumen extending axially therethrough;

a steering element secured within the lumen and adapted to displace the distal end of the housing in a lateral direction; and at least one deflection wire axially movably disposed within the lumen of the flexible housing and extending from a distal point of attachment with respect to the steering element throughout the length of the flexible housing to the proximal end thereof;

wherein axial movement of said deflection wire in a proximal direction displaces the axis of a portion of the housing in a lateral direction to facilitate steering of said device through the body cavity.

2. A steerable device as in claim 1, wherein the steering element is secured within the lumen by a solder joint disposed proximally of the distal point of attachment.

3. A steerable device as in claim 2, further comprising a wire guide for axially slidably receiving the deflection wire, and wherein the steering element is soldered to the wire guide.

4. A steerable device as in claim 3, wherein the wire guide is secured to the flexible housing.

5. A steerable device as in claim 1, wherein the distal point of attachment comprises a solder joint between the steering element and the deflection wire.

6. A steerable device as in claim 1, further comprising a safety wire extending from the distal point of attachment to the distal end of the flexible housing.

7. A steerable device as in claim 6, wherein the safety wire comprises an extension of the pull wire or of the steering element.

8. A steerable device as in claim 1, further comprising means for transmitting rotational torque between the flexible housing and the deflection wire.

9. A steerable device as in claim 1, further comprising a second deflection wire for straightening the laterally displaced portion of the housing.

10. A steerable device as in claim 1, wherein at least a portion of said deflection wire comprises a multi-filament wire.

11. A steerable device as in claim 10, wherein said multi-filament wire comprises from about three to about ten monofilament strands.

12. A steerable device as in claim 10, wherein the deflection wire comprises a solid proximal portion and a multi-filament distal portion.

13. A steerable device as in claim 12, wherein said multi-filament distal portion comprises seven strands of stainless steel wire, each strand having a diameter within the range of from about 0.0003 to about 0.002 inches.

14. A steerable device as in claim 1, wherein said deflection wire further comprises a lubricous coating.

15. A steerable device as in claim 14, wherein said lubricous coating is selected from the group consisting of polytetrafluoroethylene, polyimide, nylon and silicone.

16. A steerable device as in claim 2, wherein the length of said flexible steering element between the distal point of attachment and the solder joint is less than about 1 inch.

17. A steerable device as in claim 16, wherein said length is within the range of from about 0.010 to 0.300 inches.

18. A steerable device as in claim 16, wherein said length is within the range of from about 0.020 to 0.090 inches.

19. A steerable device as in claim 1, wherein at least a portion of said steering element is approximately rectangular in cross section.

20. A steerable device as in claim 19, wherein the rectangular portion of said steering element in its narrow cross-sectional dimension has a thickness of within the range of from about 0.0002 to about 0.010 inches.

21. A steerable device as in claim 16, wherein the cross-sectional dimensions of said steering element are about 0.001±50% inches by about 0.007±50% inches.

22. A steerable implement, comprising:
an elongate flexible housing having proximal and distal ends and a central lumen extending therebetween, the distal end of the housing being flexible in a lateral direction;
an axially extending steering element secured in the housing, and adapted to displace the distal end of the housing in said lateral direction;
at least one deflection wire having proximal and distal ends extending along the housing, said wire being secured with respect to the steering element; and
a control at the proximal end of the housing for engaging the proximal end of the deflection wire to enable said deflection wire to be displaced axially, in relation to said housing;
wherein the axis of at least a portion of the steering element is displaced laterally in response to axial displacement of the deflection wire, thereby causing the distal end of said housing to bend out of the line of the housing longitudinal axis.

23. A steerable implement as in claim 22, wherein the steering element is secured with respect to the housing at a point within about 2 cm of the distal end of the housing to form a fulcrum.

24. A steerable implement as in claim 23, wherein the elongate flexible housing is relatively axially non-compressible proximally to the fulcrum.

25. A steerable implement as in claim 24, wherein the axially non-compressible portion of the housing comprises a wire coil.

26. A steerable implement as in claim 23, wherein the flexible housing distally of the fulcrum comprises a wire coil in which the adjacent windings of wire coil are separated from one another.

27. A steerable implement as in claim 23, wherein said fulcrum comprises a tubular wire guide secured to the interior of the elongate flexible housing, and additionally secured to the steering element.

28. A steerable implement as in claim 23, wherein an extension of the steering element extends proximally of the fulcrum.

29. A steerable implement as in claim 27, wherein said deflection wire extends from the proximal end of the elongate flexible housing distally through the tubular wire guide, and at least as far as a distal point of attachment between the deflection wire and the steering element.

30. A steerable implement as in claim 29, further comprising at least one torque transmitter for transmitting rotation between the deflection wire and the tubular housing.

* * * * *